US011217341B2

(12) United States Patent
Hope et al.

(10) Patent No.: US 11,217,341 B2
(45) Date of Patent: Jan. 4, 2022

(54) FITNESS MONITORING METHODS, SYSTEMS, AND PROGRAM PRODUCTS, AND APPLICATIONS THEREOF

(71) Applicant: adidas AG, Herzogenaurach (DE)

(72) Inventors: Tony Hope, Weisendorf (DE); Stephen John Black, Portland, OR (US); Maya Ann Powch, Portland, OR (US)

(73) Assignee: adidas AG, Herzogenaurach (DE)

( * ) Notice: Subject to any disclaimer, the term of this patent is extended or adjusted under 35 U.S.C. 154(b) by 843 days.

(21) Appl. No.: 15/485,329

(22) Filed: Apr. 12, 2017

(65) Prior Publication Data
US 2017/0216676 A1    Aug. 3, 2017

Related U.S. Application Data

(63) Continuation of application No. 13/080,322, filed on Apr. 5, 2011, now abandoned.

(51) Int. Cl.
*G16H 20/30* (2018.01)
*A63B 24/00* (2006.01)

(52) U.S. Cl.
CPC ......... *G16H 20/30* (2018.01); *A63B 24/0003* (2013.01); *A63B 24/0062* (2013.01); *A63B 24/0075* (2013.01); *A63B 24/0087* (2013.01); *A63B 2225/20* (2013.01)

(58) Field of Classification Search
CPC ............ A63B 24/0075; A63B 24/0003; A63B 24/0062; A63B 24/0087; A63B 2225/20; G06F 19/3481
See application file for complete search history.

(56) References Cited

U.S. PATENT DOCUMENTS

| 3,742,937 A | 7/1973 | Manuel et al. |
| 3,802,698 A | 4/1974 | Burian et al. |
| 3,838,684 A | 10/1974 | Manuel et al. |

(Continued)

FOREIGN PATENT DOCUMENTS

| CN | 101031101 A | 9/2007 |
| CN | 101894206 A | 11/2010 |

(Continued)

OTHER PUBLICATIONS

Baca et al., "Rapid Feedback Systems for Elite Sports Training," Pervasive Computing, IEEE vol. 5, Issue: 4, 2006, pp. 70-76.

(Continued)

*Primary Examiner* — Nathan Hillery
(74) *Attorney, Agent, or Firm* — Sterne, Kessler, Goldstein & Fox P.L.L.C.

(57) ABSTRACT

Program products, methods, and systems for providing fitness monitoring are disclosed. In an embodiment, a method for scheduling training activities for a user of a fitness monitoring device includes: defining a cardio training plan including one or more cardio training activities and defining a non-cardio training plan including one or more non-cardio training activities; scheduling execution of the non-cardio training plan and the cardio training plan in a training calendar; and providing a graphical display of the training calendar including the cardio training plan and the non-cardio training plan to the user of the fitness monitoring device.

20 Claims, 35 Drawing Sheets

(56) References Cited

U.S. PATENT DOCUMENTS

| | | |
|---|---|---|
| 3,978,849 A | 9/1976 | Geneen |
| 4,027,663 A | 6/1977 | Fischler et al. |
| 4,038,976 A | 8/1977 | Hardy et al. |
| 4,120,294 A | 10/1978 | Wolfe |
| 4,120,296 A | 10/1978 | Prinz |
| 4,221,223 A | 9/1980 | Linden |
| 4,248,244 A | 2/1981 | Charnitski et al. |
| 4,252,128 A | 2/1981 | Kane |
| 4,436,096 A | 3/1984 | Dyck et al. |
| 4,647,217 A | 3/1987 | Havel |
| 4,653,498 A | 3/1987 | New, Jr. et al. |
| 4,776,323 A | 10/1988 | Spector |
| 4,788,983 A | 12/1988 | Brink et al. |
| 4,867,442 A | 9/1989 | Matthews |
| 4,938,228 A | 7/1990 | Righter et al. |
| 5,043,736 A | 8/1991 | Darnell et al. |
| 5,291,301 A | 3/1994 | Lee |
| 5,314,389 A | 5/1994 | Dotan |
| 5,334,974 A | 8/1994 | Simms et al. |
| 5,335,188 A | 8/1994 | Brisson |
| 5,400,254 A | 3/1995 | Fujita |
| 5,470,233 A | 11/1995 | Fruchterman et al. |
| 5,598,849 A | 2/1997 | Browne |
| 5,627,548 A | 5/1997 | Woo et al. |
| 5,702,323 A | 12/1997 | Poulton |
| 5,724,265 A | 3/1998 | Hutchings |
| 5,735,799 A | 4/1998 | Baba et al. |
| 5,742,509 A | 4/1998 | Goldberg et al. |
| 5,751,245 A | 5/1998 | Janky et al. |
| 5,758,313 A | 5/1998 | Shah et al. |
| 5,767,795 A | 6/1998 | Schaphorst |
| 5,769,755 A | 6/1998 | Henry et al. |
| 5,802,492 A | 9/1998 | DeLorme et al. |
| 5,825,327 A | 10/1998 | Krasner |
| 5,857,066 A | 1/1999 | Wyche et al. |
| 5,857,939 A | 1/1999 | Kaufman |
| 5,891,042 A | 4/1999 | Sham et al. |
| 5,908,464 A | 6/1999 | Kishigami et al. |
| 5,910,799 A | 6/1999 | Carpenter et al. |
| 5,919,239 A | 7/1999 | Fraker et al. |
| 5,938,721 A | 8/1999 | Dussell et al. |
| 5,948,040 A | 9/1999 | DeLorme et al. |
| 5,976,083 A | 11/1999 | Richardson et al. |
| 6,002,982 A | 12/1999 | Fry |
| 6,009,138 A | 12/1999 | Slusky |
| 6,010,430 A | 1/2000 | Mankovtiz |
| 6,011,494 A | 1/2000 | Watanabe et al. |
| 6,013,007 A | 1/2000 | Root et al. |
| 6,032,108 A | 2/2000 | Seiple et al. |
| 6,080,110 A | 6/2000 | Thorgersen |
| 6,080,111 A | 6/2000 | Pao-Lang |
| 6,104,947 A | 8/2000 | Heikkila et al. |
| 6,133,722 A | 10/2000 | Havel |
| 6,135,951 A | 10/2000 | Richardson et al. |
| 6,148,262 A | 11/2000 | Fry |
| 6,163,718 A | 12/2000 | Fabrizio |
| 6,198,431 B1 | 3/2001 | Gibson |
| 6,212,469 B1 | 4/2001 | Knepper et al. |
| 6,230,047 B1 | 5/2001 | McHugh |
| 6,244,988 B1 | 6/2001 | Delman |
| 6,246,362 B1 | 6/2001 | Tsubata et al. |
| 6,251,048 B1 | 6/2001 | Kaufman |
| 6,345,197 B1 | 2/2002 | Fabrizio |
| 6,394,960 B1 | 5/2002 | Shinogi et al. |
| 6,463,385 B1 | 10/2002 | Fry |
| 6,513,532 B2 | 2/2003 | Mault et al. |
| 6,572,636 B1 | 6/2003 | Hagen et al. |
| 6,582,342 B2 | 6/2003 | Kaufman |
| 6,585,622 B1 | 7/2003 | Shum et al. |
| 6,601,016 B1 | 7/2003 | Brown et al. |
| 6,605,038 B1 | 8/2003 | Teller et al. |
| 6,607,493 B2 | 8/2003 | Song |
| 6,611,789 B1 | 8/2003 | Darley |
| 6,716,139 B1 | 4/2004 | Hosseinzadeh-Dolkhani et al. |
| 6,734,837 B1 | 5/2004 | Havel |
| 6,736,759 B1 | 5/2004 | Stubbs et al. |
| 6,741,927 B2 | 5/2004 | Jones |
| 6,745,069 B2 | 6/2004 | Nissila et al. |
| 6,746,370 B1 | 6/2004 | Fleming et al. |
| 6,746,371 B1 | 6/2004 | Brown et al. |
| 6,753,882 B2 | 6/2004 | Nakazawa et al. |
| 6,758,816 B1 | 7/2004 | Tsubata et al. |
| 6,790,178 B1 | 9/2004 | Mault et al. |
| 6,798,378 B1 | 9/2004 | Walters |
| 6,823,036 B1 | 11/2004 | Chen |
| 6,832,109 B2 | 12/2004 | Nissila |
| 6,837,827 B1 | 1/2005 | Lee et al. |
| 6,845,321 B1 | 1/2005 | Kerns |
| 6,853,955 B1 | 2/2005 | Burrell et al. |
| 6,872,077 B2 | 3/2005 | Yeager |
| 6,879,285 B2 | 4/2005 | Nobukiyo |
| 6,882,955 B1 | 4/2005 | Ohlenbusch et al. |
| 6,918,858 B2 | 7/2005 | Watterson et al. |
| 6,921,351 B1 | 7/2005 | Hickman et al. |
| 7,057,551 B1 | 6/2006 | Vogt |
| 7,062,225 B2 | 6/2006 | White |
| 7,070,539 B2 | 7/2006 | Brown et al. |
| 7,076,291 B2 | 7/2006 | Pulkkinen et al. |
| 7,081,809 B1 | 7/2006 | Mix et al. |
| 7,085,678 B2 | 8/2006 | Burrell et al. |
| 7,097,588 B2 | 8/2006 | Watterson et al. |
| 7,172,530 B1 | 2/2007 | Hercules |
| 7,192,402 B2 | 3/2007 | Amano et al. |
| 7,216,034 B2 | 5/2007 | Vitikainen et al. |
| 7,217,224 B2 | 5/2007 | Thomas |
| 7,220,220 B2 | 5/2007 | Stubbs et al. |
| 7,229,385 B2 | 6/2007 | Freeman et al. |
| 7,251,454 B2 | 7/2007 | White |
| 7,254,516 B2 | 8/2007 | Case, Jr. et al. |
| 7,257,517 B2 | 8/2007 | Shitan |
| 7,264,554 B2 | 9/2007 | Bentley |
| 7,292,867 B2 | 11/2007 | Werner et al. |
| 7,383,081 B2 | 6/2008 | Butt et al. |
| 7,398,151 B1 | 7/2008 | Burrell et al. |
| 7,428,471 B2 | 9/2008 | Darley et al. |
| 7,428,472 B2 | 9/2008 | Darley et al. |
| 7,466,992 B1 | 12/2008 | Fujisaki |
| 7,480,512 B2 | 1/2009 | Graham et al. |
| 7,518,054 B2 | 4/2009 | McKinney et al. |
| 7,519,327 B2 | 4/2009 | White |
| 7,603,255 B2 | 10/2009 | Case, Jr. et al. |
| 7,643,895 B2 | 1/2010 | Gupta et al. |
| 7,648,463 B1 | 1/2010 | Gupta et al. |
| 7,670,263 B2 | 3/2010 | Ellis et al. |
| 7,689,283 B1 | 3/2010 | Bentley |
| 7,706,815 B2 | 4/2010 | Graham et al. |
| 7,717,827 B2 | 5/2010 | Kurunmaki et al. |
| 7,766,794 B2 | 8/2010 | Oliver et al. |
| 7,771,320 B2 | 8/2010 | Riley et al. |
| 7,805,149 B2 | 9/2010 | Werner et al. |
| 7,805,150 B2 | 9/2010 | Graham et al. |
| 7,909,737 B2 | 3/2011 | Ellis et al. |
| 7,921,163 B1 | 4/2011 | Odell et al. |
| 7,951,046 B1 | 5/2011 | Barber, Jr. |
| 7,985,164 B2 | 7/2011 | Ashby |
| 8,001,472 B2 | 8/2011 | Gilley et al. |
| 8,052,580 B2 | 11/2011 | Saalasti et al. |
| 8,068,858 B2 | 11/2011 | Werner et al. |
| 8,105,208 B2 | 1/2012 | Oleson et al. |
| 2001/0003542 A1 | 6/2001 | Kita |
| 2001/0027375 A1 | 10/2001 | Machida et al. |
| 2002/0049535 A1 | 4/2002 | Rigo et al. |
| 2002/0068873 A1 | 6/2002 | Nissila |
| 2002/0094776 A1 | 7/2002 | Pulver |
| 2002/0102988 A1 | 8/2002 | Myllymaki |
| 2002/0107433 A1 | 8/2002 | Mault |
| 2003/0069108 A1 | 4/2003 | Kaiserman et al. |
| 2003/0091964 A1 | 5/2003 | Yeager |
| 2003/0100315 A1 | 5/2003 | Rankin |
| 2003/0171189 A1 | 9/2003 | Kaufman |
| 2003/0191578 A1 | 10/2003 | Paulauskas et al. |
| 2003/0208409 A1 | 11/2003 | Mault |
| 2003/0224337 A1 | 12/2003 | Shum et al. |
| 2003/0229446 A1 | 12/2003 | Boscamp et al. |

(56) References Cited

U.S. PATENT DOCUMENTS

| | | |
|---|---|---|
| 2004/0046692 A1 | 3/2004 | Robson et al. |
| 2004/0102931 A1 | 5/2004 | Ellis et al. |
| 2004/0116784 A1 | 6/2004 | Gavish |
| 2004/0171956 A1 | 9/2004 | Babashan |
| 2004/0199056 A1 | 10/2004 | Husemann et al. |
| 2004/0203789 A1 | 10/2004 | Hammond et al. |
| 2004/0203873 A1 | 10/2004 | Gray |
| 2004/0240946 A1 | 12/2004 | Haun |
| 2004/0249846 A1 | 12/2004 | Randall et al. |
| 2005/0049113 A1 | 3/2005 | Yuch et al. |
| 2005/0075214 A1 | 4/2005 | Brown et al. |
| 2005/0079905 A1 | 4/2005 | Martens |
| 2005/0096933 A1 | 5/2005 | Collins, III et al. |
| 2005/0121504 A1 | 6/2005 | Sanders et al. |
| 2005/0124463 A1 | 6/2005 | Yeo et al. |
| 2005/0172311 A1 | 8/2005 | Hjelt et al. |
| 2005/0177059 A1 | 8/2005 | Koivumaa et al. |
| 2005/0195094 A1 | 9/2005 | White |
| 2005/0197063 A1 | 9/2005 | White |
| 2005/0209050 A1 | 9/2005 | Bartels |
| 2005/0209887 A1 | 9/2005 | Pollner |
| 2005/0256416 A1 | 11/2005 | Chen |
| 2005/0266961 A1 | 12/2005 | Shum et al. |
| 2005/0287499 A1 | 12/2005 | Yeager |
| 2006/0025282 A1 | 2/2006 | Redmann |
| 2006/0063980 A1 | 3/2006 | Hwang et al. |
| 2006/0082472 A1 | 4/2006 | Adachi et al. |
| 2006/0136173 A1 | 6/2006 | Case, Jr. et al. |
| 2006/0156356 A1 | 7/2006 | Sato et al. |
| 2006/0169125 A1 | 8/2006 | Ashkenazi et al. |
| 2006/0189360 A1 | 8/2006 | White |
| 2006/0240865 A1 | 10/2006 | White |
| 2006/0252602 A1 | 11/2006 | Brown et al. |
| 2006/0253210 A1 | 11/2006 | Rosenberg |
| 2007/0006489 A1 | 1/2007 | Case, Jr. et al. |
| 2007/0011919 A1 | 1/2007 | Case, Jr. |
| 2007/0021269 A1 | 1/2007 | Shum |
| 2007/0033069 A1 | 2/2007 | Freeman et al. |
| 2007/0135225 A1 | 6/2007 | Nieminen et al. |
| 2007/0159926 A1 | 7/2007 | Prstojevich et al. |
| 2007/0208531 A1 | 9/2007 | Darley et al. |
| 2007/0219059 A1 | 9/2007 | Schwartz et al. |
| 2007/0232455 A1 | 10/2007 | Hanoun |
| 2007/0260421 A1 | 11/2007 | Berner et al. |
| 2007/0265138 A1 | 11/2007 | Ashby |
| 2007/0287596 A1 | 12/2007 | Case, Jr. et al. |
| 2008/0002528 A1 | 1/2008 | Andren et al. |
| 2008/0004510 A1 | 1/2008 | Tanzawa et al. |
| 2008/0009275 A1 | 1/2008 | Werner et al. |
| 2008/0051201 A1 | 2/2008 | Lore |
| 2008/0051993 A1 | 2/2008 | Graham et al. |
| 2008/0058971 A1 | 3/2008 | Graham et al. |
| 2008/0059064 A1 | 3/2008 | Werner et al. |
| 2008/0065319 A1 | 3/2008 | Graham et al. |
| 2008/0076637 A1 | 3/2008 | Gilley et al. |
| 2008/0096726 A1* | 4/2008 | Riley ............. A63B 24/0006 482/8 |
| 2008/0101161 A1 | 5/2008 | Imai et al. |
| 2008/0103689 A1 | 5/2008 | Graham et al. |
| 2008/0171636 A1 | 7/2008 | Usui et al. |
| 2008/0200310 A1 | 8/2008 | Taliabue |
| 2008/0319661 A1 | 12/2008 | Werner et al. |
| 2009/0047645 A1 | 2/2009 | Dibenedetto et al. |
| 2009/0048044 A1 | 2/2009 | Oleson et al. |
| 2009/0048070 A1 | 2/2009 | Vincent et al. |
| 2009/0069156 A1 | 3/2009 | Kurunmaki et al. |
| 2009/0233770 A1 | 9/2009 | Vincent et al. |
| 2009/0292178 A1 | 11/2009 | Ellis et al. |
| 2010/0042427 A1 | 2/2010 | Graham et al. |
| 2010/0045463 A1 | 2/2010 | Bradley et al. |
| 2010/0062818 A1 | 3/2010 | Haughay et al. |
| 2010/0075806 A1 | 3/2010 | Mongtomery |
| 2010/0088023 A1 | 4/2010 | Werner |
| 2010/0129780 A1 | 5/2010 | Homsi et al. |
| 2010/0184563 A1 | 7/2010 | Molyneux et al. |
| 2010/0184564 A1 | 7/2010 | Molyneux et al. |
| 2010/0216601 A1 | 8/2010 | Saalasti et al. |
| 2010/0292050 A1 | 11/2010 | Oleson et al. |
| 2010/0292599 A1 | 11/2010 | Oleson et al. |
| 2010/0292600 A1* | 11/2010 | DiBenedetto ...... A63B 24/0062 600/520 |
| 2010/0311544 A1 | 12/2010 | Robinette et al. |
| 2011/0082641 A1 | 4/2011 | Werner et al. |
| 2011/0087137 A1 | 4/2011 | Hanoun |
| 2011/0098156 A1 | 4/2011 | Ng et al. |
| 2012/0258433 A1 | 10/2012 | Hope et al. |

FOREIGN PATENT DOCUMENTS

| | | |
|---|---|---|
| DE | 3320502 A1 | 12/1983 |
| GB | 2257558 A | 1/1993 |
| JP | 63144286 | 6/1988 |
| JP | 10329452 | 12/1998 |
| JP | 2002/248187 | 9/2002 |
| JP | 2002/288381 | 10/2002 |
| JP | 2004/247954 | 9/2004 |
| JP | 2006263002 A | 10/2006 |
| JP | 2007-507256 A | 3/2007 |
| JP | 2007312246 | 11/2007 |
| WO | WO 02067449 | 8/2002 |
| WO | WO 2007/069014 | 6/2007 |
| WO | WO 080101168 A2 | 8/2008 |
| WO | WO 08119266 | 10/2008 |
| WO | WO 09033034 | 3/2009 |

OTHER PUBLICATIONS

Basari et al., "Field Measurement on Simple Vehicle-Mounted Antenna System Using a Geostationary Satellite," Vehicular Technology, IEEE Transactions vol. 59 , Issue: 9, 2010, pp. 4248-4255.

Cavallo et al., "A step toward GPS/INS personal navigation systems: real-time assessment of gait by foot inertial sensing," Intelligent Robots and Systems, 2005, pp. 1187-1191.

Garmin International, Inc., "GPSII, Garmin Owner's Manual & Reference," Garmin Corp., Kansas, USA, Aug. 1996, 108 pages.

Garmin International, Inc., "GPSIII, Garmin Owner's Manual & Reference," Garmin Corp., Kansas, USA, Aug. 1997, 100 pages.

Garmin International, Inc., "NAVTALK Cellular Phone/GPS Receiver Owner's Manual and Reference Guide," Garmin Corporation, 1999-2000, 128 pages.

Garmin LTD, NAVTALK, Product Information, 2002, 6 pages.

Li et al., "Hierarchical Cluster Analysis on Coolmax/Cotton Double-faced Effect Knitted Fabric's Subjective Sensations in Different Sports Conditions," Information Science and Engineering, ISISE '08, International Symposium, vol. 1, 2008, pp. 622-625.

Llosa et al., "Design of a Motion Detector to Monitor Rowing Performance Based on Wireless Sensor Networks," Intelligent Networking and Collaborative Systems, 2009, pp. 397-400.

Lodha et al., "Consistent visualization and querying of GIS databases by a location-aware mobile agent," Computer Graphics International, Jul. 2003, pp. 248-253.

Losada et al., "OISTI (an Oral-Interface System to provide Tourist-Information inside a car)," Proceedings of the International Conference on Information Technology: Coding and Computing, Apr. 2001, pp. 373-377.

Magellan Systems Corporation, "Magellan GPS, NAVDLX-10 User Guide," 1995, 91 pages.

Magellan Systems Corporation, "Magellen GPS Satellite Navigator Reference Guide Trailblazer XL," 1995, 78 pages.

Malkinson, T., "Current and emerging technologies in endurance athletic training and race monitoring," Science and Technology for Humanity (TIC-STH), 2009 IEEE Toronto International Conference, 2009, pp. 581-586.

Mann, S., "WearCam (The wearable camera): personal imaging systems for long-term use in wearable tetherless computer-mediated reality and personal photo/videographic memory prosthesis," Wearable Computers, 1998. Digest of Papers; Second International Symposium on, Oct. 19-20, 1998, pp. 124-131.

(56) References Cited

OTHER PUBLICATIONS

Mehaffey et al., "Garmin's NavTalk Cell Phone and Road Map GPS Product Review" Revision 2, Nov. 2, 1999, 5 pgs.

Sawhney et al., "Speaking and Listening on the Run: Design for Wearable Audio Computing," Speech Interface Group, MIT Media Laboratory, Oct. 19-20, 1998, 11 pages.

Silva et al., "Homogeneous access to temporal data and interaction histories in visual interface for databases," User Interfaces to Data Intensive Systems, 1999, pp. 108-117.

Svendsen et al., "Adaptive antenna for handheld GPS receivers," Position Location and Navigation Symposium (PLANS), 2010, pp. 436-442.

Waegli et al., "Redundant MEMS-IMU integrated with GPS for performance assessment in sports," Position, Location and Navigation Symposium, 2008, pp. 1260-1268.

Wei et al., "A self-coherence anti-jamming GPS receiver," Signal Processing vol. 53, Issue 10, Part 1, Oct. 2005, pp. 3910-3915.

\* cited by examiner

FIG. 19

Intro to Training : Sample Workout - 24 - 00:25:00

⊗ CLOSE

| Overview | Pillar Prep | Movement Prep | Plyometric | Strength | Regeneration |

219 ─ 219 ─ 219 ─

I'M DONE

○ STRENGTH / 00:10:00 / 10 EXERCISES

1

PULL UP - NEUTRAL GRIP
Pullup Bar

[WATCH AND LEARN]

| | REPS / TIME | WEIGHT |
|---|---|---|
| | 10 reps | --- |

2 - CIRCUIT ⓘ

PULL UP - NEUTRAL GRIP
Pullup Bar

[WATCH AND LEARN]

RDL - DB
Free Weight

[WATCH AND LEARN]

90/90 STRETCH
No Equipment

[WATCH AND LEARN]

| | REPS / TIME | WEIGHT |
|---|---|---|
| Set 1 | 15 reps | 10 lbs |
| Set 2 | 15 reps | 10 lbs |
| Set 3 | 15 reps | 5 lbs |
| Set 1 | 15 reps | 10 lbs |
| Set 2 | 15 reps | 10 lbs |
| Set 3 | 15 reps | 5 lbs |
| Set 1 | 15 reps | 10 lbs |
| Set 2 | 15 reps | 10 lbs |
| Set 3 | 15 reps | 5 lbs |

Welcome, Tony! Log Out | Messages | Settings | Downloads | Help | Feedback | Legal

| ▶ Explore | ▶ Plan | ▶ Manage | ▶ Track | Forum |

HIP REC... ⊗ CLOSE ⊙ GO BACK

SET UP WORKOUT LOAD

Please select the option that best describes your current abilities. If you are familiar with training with weights and know specific values for specific movements, you can fine tune your workout by providing that information in your Workout Load settings.

What is the maximum weight you can bench press 10 times in a row (1 set of 10 reps)?

◉ I don't know   ○ 10-20 lbs   ○ 21-50 lbs   ○ 50-100 lbs   ○ 100+ lbs

What is the maximum weight you can military press 10 times in a row (1 set of 10 reps)?

◉ I don't know   ○ 10-20 lbs   ○ 21-50 lbs   ○ 50-100 lbs   ○ 100+ lbs

What is the maximum weight you can bench press 30 times in a row (1 set of 10 reps)?

◉ I don't know   ○ 10-20 lbs   ○ 21-50 lbs   ○ 50-100 lbs   ○ 100+ lbs

Workout L...
This pack
workout load settings. You might want to review and update them before you start.   APPLY PACK TO MY SCHEDULE

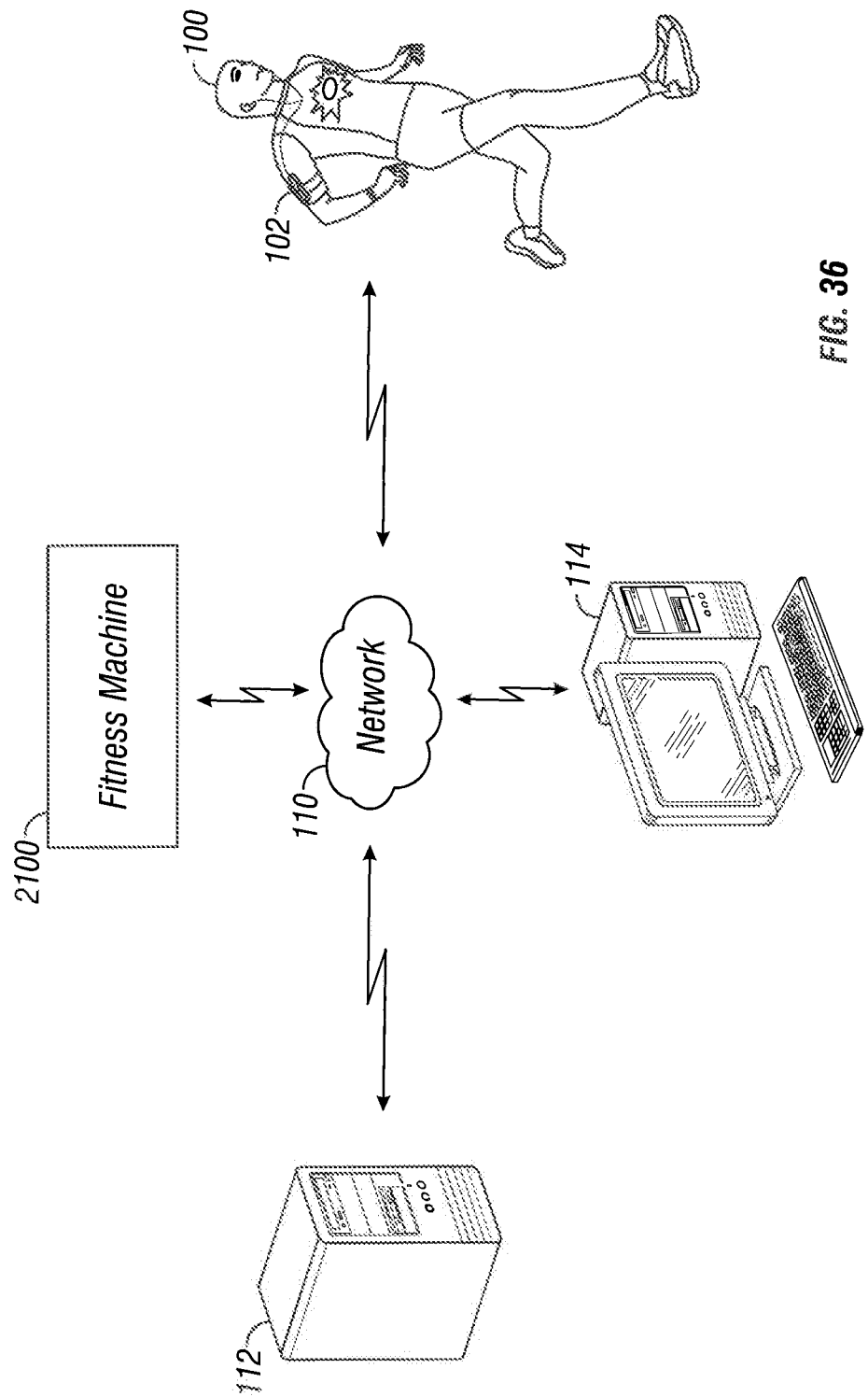

FITNESS MONITORING METHODS, SYSTEMS, AND PROGRAM PRODUCTS, AND APPLICATIONS THEREOF

CROSS-REFERENCE TO RELATED APPLICATIONS

This application is a continuation of U.S. patent application Ser. No. 13/080,322, filed Apr. 5, 2011. The contents of this application are expressly incorporated herein by reference thereto in their entireties, for all purposes.

FIELD OF THE INVENTION

The present invention generally relates to fitness monitoring. More particularly, the present invention relates to program products, methods, and systems for providing fitness monitoring.

BACKGROUND OF THE INVENTION

Exercise is important to maintaining a healthy lifestyle and individual well-being. Accordingly, many individuals want to participate in an exercise program. The most successful exercise programs are ones tailored to a fitness level of an individual and aimed at assisting the individual to achieve one or more specific fitness or exercise goals.

Sports trainers, as well as other exercise and fitness professionals, are available to assist individuals in developing exercise programs appropriate for their individual fitness levels and their specific fitness or exercise goals. Hiring such professionals, however, can be expensive. Furthermore, the busy schedules of many individuals make it difficult for these individuals to set aside time to meet with an exercise and fitness professional on a routine basis. Thus, many individuals forego using the services of exercise and fitness professionals, and they never achieve the benefits that can be obtained from an exercise program tailored, for example, to one's fitness level.

Technology has resulted in the development of systems capable of transferring performance information obtained from a user during a workout to a remote computer for further analysis, and systems capable of creating a schedule of training activities for the user. These systems often provide a user interface that allows the user to review their past performance data and schedule future training activities.

What is needed are improved program products, methods, and systems for providing fitness monitoring that will allow athletes to, among other things, better use data generated from past performances to gauge their improvement, to schedule activities and set goals for the future, to share their performance data with others, to stay motivated, and/or to enable them to exercise at intensities appropriate for their current fitness level and goals.

BRIEF SUMMARY OF THE INVENTION

Embodiments of the present invention relate to a method for scheduling training activities for a user of a fitness monitoring device, including the steps of: defining a cardio based training plan including one or more cardio based training activities and a non-cardio based training plan including one or more non-cardio based training activities; scheduling execution of the non-cardio training plan and the cardio training plan in a training calendar; and providing a graphical display of the training calendar including the cardio training plan and the non-cardio training plan to the user at the fitness monitoring device and/or at a computer. In one embodiment, the method includes providing coaching to the user about the cardio training activity. In another embodiment, the method includes providing coaching to the user about the cardio training activity and the non-cardio training activity. In another embodiment, the method includes providing coaching to the user about the non-cardio training activity.

In another embodiment, a tangible computer program product for scheduling training activities for a user of a fitness monitoring device comprises a computer readable medium having computer program logic recorded thereon for causing at least one processor to: define a cardio based training plan including one or more cardio based training activities and a non-cardio based training plan including one or more strength based training activities; schedule execution of the strength training activity based on a scheduling of the cardio training activity; and provide a graphical display of a schedule including the cardio training activity and the strength training activity to the user at the fitness monitoring device and/or at a computer.

In yet another embodiment, a method for scheduling training activities for a user of a fitness monitoring device, comprises the steps of: receiving a training category selection from the user; scheduling a plurality of training activities based on the selected training category, wherein a first training activity requires execution of a plurality of body movements with a first resistance goal; receiving input from the user about the first resistance goal after completion of the first training activity; and defining a second resistance goal of a second training activity based on the received user input.

In another embodiment a method for generating a workout routine for an athlete, includes: receiving a training category selection from a portable fitness monitoring device and/or computer, receiving performance information associated with the athlete from the portable fitness monitoring device; generating a schedule of a plurality of training activities based on the selected training category and the performance information, wherein a first scheduled training activity includes a cardio goal and a second scheduled training activity includes a resistance goal; and sending the schedule to the portable fitness monitoring device and/or a personal computer, for example. Each of the steps of the method may be executed using at least one processor.

Embodiments may include systems and methods for creating and scheduling a training plan on one or both of a portable fitness monitoring device and a computer, which may be remote from the portable fitness monitoring device.

Embodiments may include a server and one or more fitness monitoring devices and sensors in communication with the server. The one or more fitness monitoring devices and sensors may communicate with each other and with a training module for creating and scheduling a training plan.

Further embodiments, features, and technical advantages of the present invention, as well as the structure and operation of the various embodiments of the present invention, are described in detail below with reference to the accompanying drawings.

BRIEF DESCRIPTION OF THE DRAWINGS/FIGURES

The accompanying drawings, which are incorporated herein and form a part of the specification, illustrate the present invention by way of example, and not by way of limitation, and, together with the description, further serve to explain the principles of the invention and to enable a person skilled in the pertinent art to make and use the invention.

FIG. 19 is an exemplary GUI window including an exemplary workout according to an embodiment of the present invention.

FIG. 20 is an exemplary GUI window including an exemplary workout according to an embodiment of the present invention.

FIG. 23 is an exemplary GUI window for generating a workout schedule according to an embodiment of the present invention.

FIG. 25 is an exemplary GUI window for user input according to an embodiment of the present invention.

FIG. 26 is an exemplary GUI window depicting a user workout schedule according to an embodiment of the present invention.

FIG. 27 is an exemplary GUI window according to an embodiment of the present invention.

FIG. 29 is an exemplary GUI window for user input of actual completed workout data according to an embodiment of the present invention.

FIG. 36 is an illustration of a fitness monitoring device and a training module in communication with a fitness machine according to an embodiment of the present invention.

DETAILED DESCRIPTION OF THE INVENTION

Figure 1:
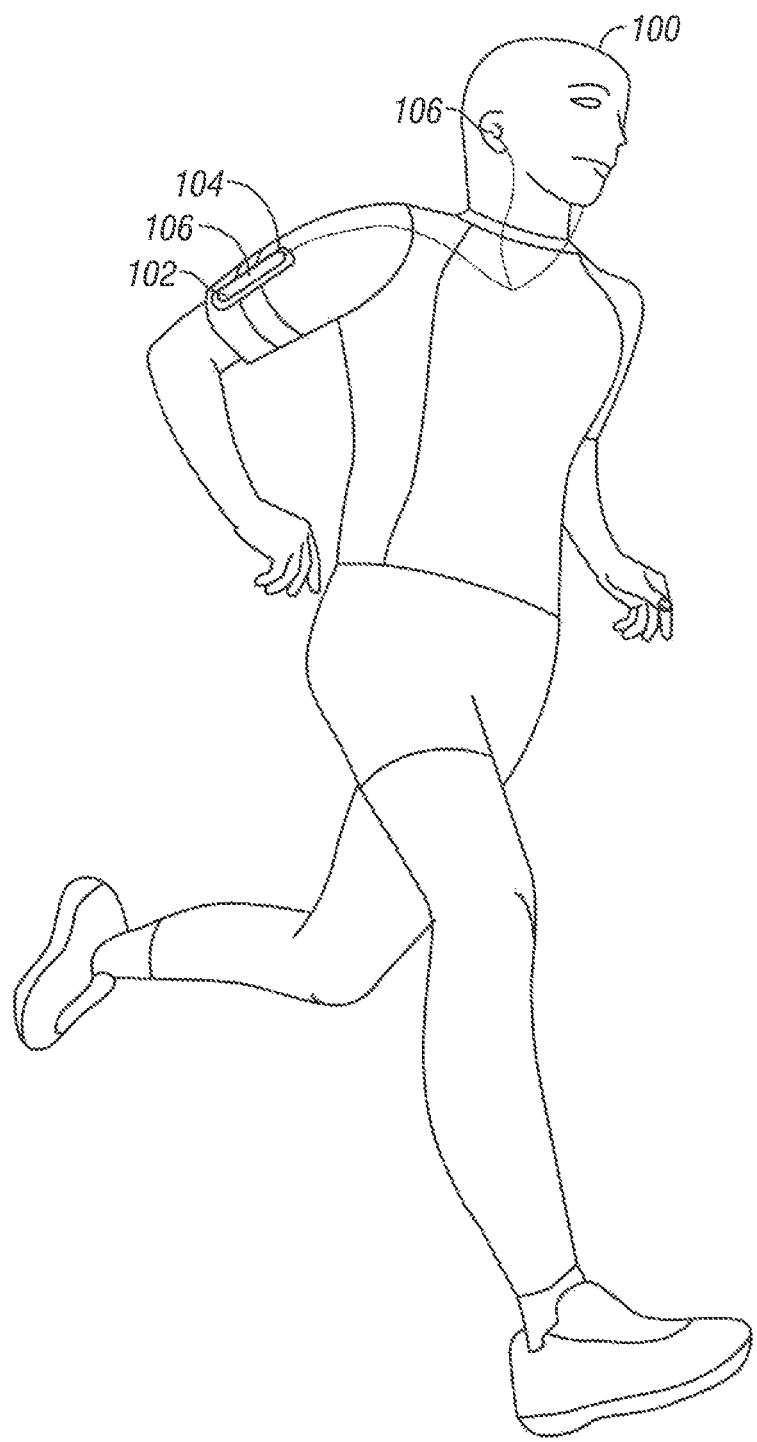
FIG. 1 is an illustration of an athlete engaged in an activity according to an embodiment of the present invention.

The present invention will now be described in detail with reference to embodiments thereof as illustrated in the accompanying drawings. References to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Furthermore, while the term "user" may include an athlete who conducts a physical activity, the term "user" may also be used herein to refer to a user other than the athlete conducting the physical activities of interest. In other words, other users in addition to the athlete-user, such as coaches or friends or family, may be able to interact with the systems and methods of the present invention. In some embodiments, the user may be the athlete.

In general, the methods, systems, and program products of the present invention may be used to provide fitness monitoring to athletes. In at least some embodiments of the present invention, a portable fitness monitoring device and a computer server system may interact with one another to provide the fitness monitoring methods.

In one embodiment, the athlete may utilize the portable fitness monitoring device during a physical activity. In another embodiment, the athlete may interact with the computer server system before, during, and/or after the physical activity.

The portable fitness monitoring device may be adapted to measure various performance parameters associated with the athlete's physical activities, to provide feedback to the athlete during the activities, to send information to the server system, and/or to receive information from the server system. The server system may be adapted to process performance information associated with the athlete's activities, to provide feedback to the athlete before, during, and/or after the physical activities, to send information to the portable fitness monitoring device, and/or to receive information from the portable fitness monitoring device. In one embodiment, performance parameters associated with the athlete's physical activities may be received and viewed by an authorized individual (e.g., a coach) in real-time or substantially in real-time. Based on this information, the coach may also provide feedback to the athlete during the activity.

In one embodiment, a portable fitness monitoring device and a computer server system may interact with one another via a wireless wide area network. In another embodiment, the server system may present information to the athlete via the athlete's portable fitness monitoring device. In a further embodiment, the server system may present information to a user (who may or may not be the athlete) via a remote computer (which may or may not be the portable fitness monitoring device).

In one exemplary embodiment of the present invention, the athlete may interact with the portable fitness monitoring device and the server system in various ways at various times as follows.

First, prior to engaging in a physical activity, the athlete may access a website provided by the server from a remotely located personal computer. The athlete stationed at the remotely located personal computer may use the website to plan and schedule a prospective physical activity. Alternatively, the athlete may plan and schedule a prospective physical activity by accessing the website from the athlete's portable fitness monitoring device. In one embodiment, the version of the website accessible from the athlete's portable fitness monitoring device may be simplified or otherwise modified to optimize it for display on a relatively small screen, such as, for example, as a mobile application or "app". As will be appreciated, a user may select the mobile application of the planning, scheduling, and fitness monitoring methods by selecting, for example, an icon on the athlete's portable fitness monitoring device. For example, the user's touch or a touch gesture on the icon may initiate the application.

Next, the athlete may engage in the planned scheduled activity while utilizing the portable fitness monitoring device. Alternatively, the athlete may engage in an unplanned, unscheduled activity. During the activity, the portable fitness monitoring device may measure various performance parameters associated with the athlete's physical activity and provide feedback to the athlete during the activity. Some of the feedback provided to the athlete during the activity may depend on information received from the server before or during the activity. The portable fitness monitoring device may also send information to the server about the athlete's performance before, during, or after the activity.

Finally, after completing the activity, the athlete may again access the website provided by the server from the remotely located personal computer. The athlete stationed at the remotely located personal computer may use the website to review and analyze performance information associated with the activity. Alternatively, the athlete may review and analyze performance information associated with the activity by accessing the website from the athlete's portable fitness monitoring device. In one embodiment, the version of the website accessible from the athlete's portable fitness monitoring device may be simplified or otherwise modified to optimize it for operation and display on a relatively small screen, such as, for example, as a mobile application or "app" for a smartphone. As will be appreciated, a user may select the mobile application of the planning, scheduling, and fitness monitoring methods by selecting, for example, an icon on the athlete's portable fitness monitoring device. For example, the user's touch or a touch gesture on the icon may initiate the application.

At various points before, during, or after the activity, processors of the portable fitness monitoring device and/or the server may receive, process, send and/or display a variety of data relating to the athlete's performance.

Athletes 100 who utilize embodiments of the present invention may actively participate in a variety of physical activities including, but not limited to, basketball, tennis, football, soccer, recreational running, walking, skating, swimming, performing aerobic exercises, weight lifting, general fitness, baseball, boxing, hockey, field hockey, rugby, crew/rowing, race running, sprint running, cycling, lacrosse, golf, martial arts, gymnastics, wrestling, yoga, skiing, paddle boarding, and snowboarding, or participating in various individual or team sports. Accordingly, terms such as, for example, "athlete," "runner," and "individual" may be referred to herein interchangeably, and may generally refer to any person who conducts a physical activity in accordance with embodiments of the present invention.

More detailed examples of embodiments of the present invention that may utilize a portable fitness monitoring device and/or a computer server system to provide fitness monitoring methods to athletes are provided below.

Figure 2:
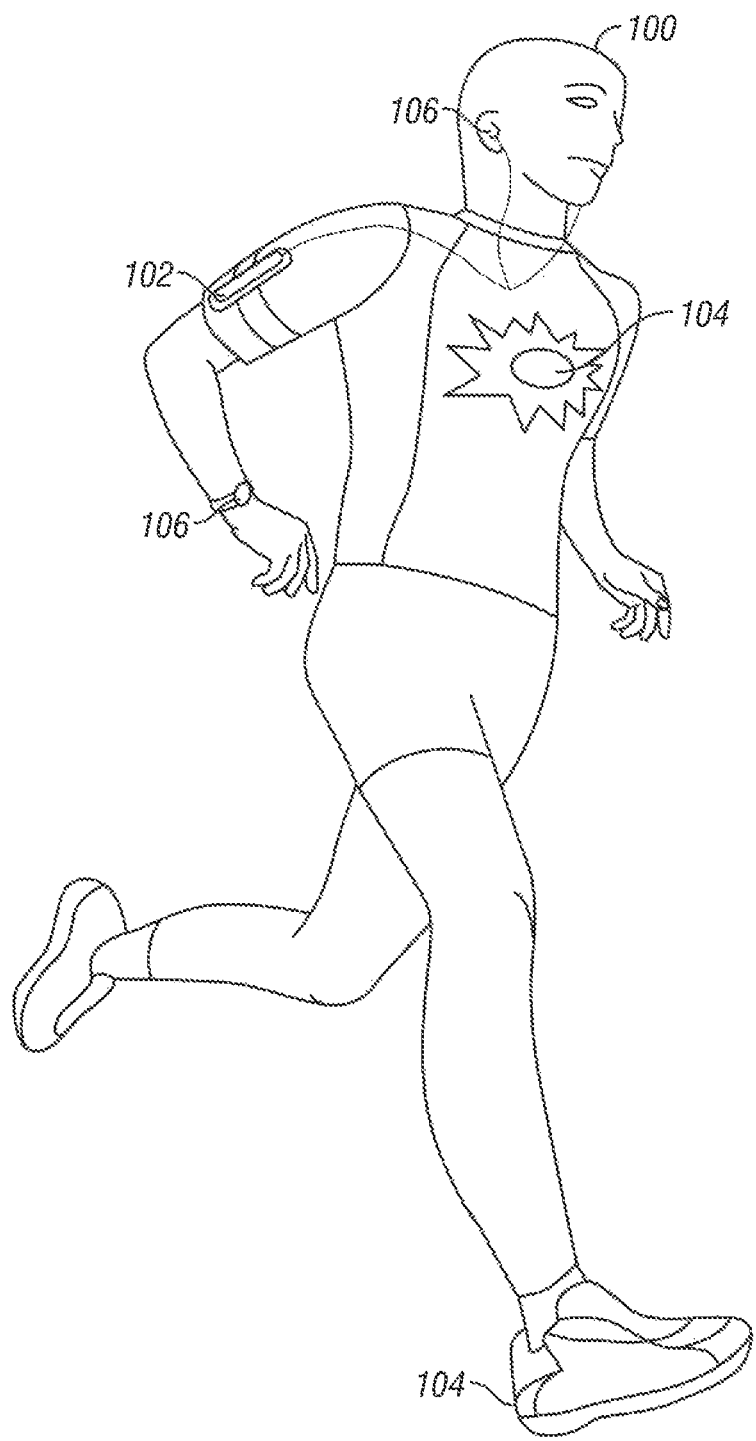
FIG. 2 is an illustration of an athlete engaged in an activity according to an embodiment of the present invention.

As illustrated in FIGS. 1 and 2, an athlete 100 engaged in physical activity may be equipped with a portable fitness monitoring device 102. The portable fitness monitoring device 102 may be worn, carried, or otherwise supported by the athlete 100 during the physical activity. The portable fitness monitoring device 102 may be adapted to measure and/or calculate various performance parameters associated with the athlete's 100 physical activity. The term "performance parameters" may include both physical parameters and physiological parameters associated with the athlete's 100 physical activity. Physical parameters measured and/or calculated may include, for example, time, location, distance, speed, pace, stride count, stride length, stride rate, and/or elevation. Physiological parameters measured and/or calculated may include, for example, heart rate, respiration rate, blood oxygen level, blood flow, hydration status, calories burned, muscle fatigue, and/or body temperature.

In an embodiment, performance parameters may also include mental or emotional parameters such as, for example, stress level or motivation level. Mental and emotional parameters may be measured and/or calculated directly or indirectly either through posing questions to the athlete 100 or by measuring things such as, for example, trunk angle or foot strike characteristics while running.

The portable fitness monitoring device 102 may be a device such as, for example, a mobile phone, a smartphone, a personal digital assistant, a music file player (e.g. and MP3 player), a tablet computer, an intelligent article for wearing (e.g. a fitness monitoring garment, wrist band, or watch), a dongle (e.g. a small hardware device that is capable of physically coupling to a first electronic device and/or wirelessly coupling to additional electronic devices), or any other suitable dedicated or non-dedicated portable fitness monitoring device 102. Suitable devices may include, for example, the devices disclosed in commonly owned U.S. patent application Ser. No. 11/892,023, titled "Sports Electronic Training System, and Applications Thereof." and commonly owned U.S. patent application Ser. No. 12/467,944, titled "Portable Fitness Monitoring Systems, and Applications Thereof," the disclosure of each of which is incorporated herein by reference in its entirety.

The portable fitness monitoring device 102 may include or communicate with one or more sensors 104 for detecting information used to measure and/or calculate performance parameters. In one embodiment of the present invention, as shown in FIG. 1, the portable fitness monitoring device 102 itself may include a sensor 104. In other words, the sensor 104 may be integrally coupled to and/or included within the same housing as the portable fitness monitoring device 102. Such a sensor 104 may be, for example, a sensor 104 for detecting information that may be used to measure and/or calculate the athlete's 100 location, distance traveled, pace and/or speed.

In another embodiment, sensors 104 may be physically separate from the portable fitness monitoring device 102. In other words, these sensors 104 may not be integrally coupled to or included within the same housing as the portable fitness monitoring device 102. In contrast, in such an embodiment, these sensors 104 may be in wired or wireless communication with the portable fitness monitoring device 102. For example, in the embodiment of FIG. 2, a sensor 104 for detecting information that may be used to measure and/or calculate the athlete's 100 heart rate is coupled to the athlete's 100 chest, while a sensor 104 for detecting information that may be used to measure and/or calculate the athlete's 100 distance traveled and/or speed is coupled to the athlete's 100 shoe.

Suitable sensors 104 may include, but not be limited to, positioning system receivers (e.g. GPS receivers or beacons), accelerometers, pedometers, pulsimeters, breath rate sensor, gyroscope, magnetometer, hydration sensor, thermometers, or other sensors 104 for detecting information that may be used to measure and/or calculate performance parameters.

The portable fitness monitoring device 102 may include or communicate with one or more portable output devices 106. The output devices 106 may be adapted to convey information to the athlete 100 in a variety of ways such as, for example, visually, audibly, and/or tactilely (e.g. via a vibrating element), either alone or in combination.

In some embodiments of the present invention, the portable fitness monitoring device 102 itself may include an output device 106. In other words, the output device 106 may be integrally coupled to and/or included within the same housing as the portable fitness monitoring device 102. In other embodiments, the output device 106 may be physically separate from the portable fitness monitoring device 102. In other words, the output device 106 may not be integrally coupled to or included within the same housing as the portable fitness monitoring device 102. In contrast, in such embodiments, the output device 106 may be in wired or wireless communication with the portable fitness monitoring device 102. In still further embodiments, the portable fitness monitoring system may include multiple portable output devices 106.

In one embodiment of the present invention, as shown in FIG. 1, the portable fitness monitoring device 102 itself may include a visual display output device 106, while a separate audible output device 106 (e.g. headphones or a speaker) may be in wired or wireless communication with the portable fitness monitoring device 102.

In another embodiment, as shown in FIG. 2, while the portable fitness monitoring device 102 itself does include an output device 106, a separate output device 106 (e.g. a wrist band having a visual display) may be in wireless communication with the portable fitness monitoring device 102. In addition, a separate audible output device 106 (e.g. headphones) may be in wired or wireless communication with the portable fitness monitoring device 102.

In embodiments where a separate visual display output device 106 is provided, the separate visual display output device 106 may take many different forms. For example, the separate portable visual display output device 106 may be a wrist watch. As a further example, in one embodiment, the separate portable visual display output device 106 may be a wristband having one or more visual displays, such as the devices disclosed in U.S. patent application Ser. No. 12/467,948, titled "Portable Fitness Monitoring Systems with Displays, and Applications Thereof," the disclosure of which is incorporated herein by reference in its entirety. The separate visual display output device 106 may be capable of displaying, for example, numerical performance parameter information or color-coded performance zone related information, as described in further detail below.

Figure 3:
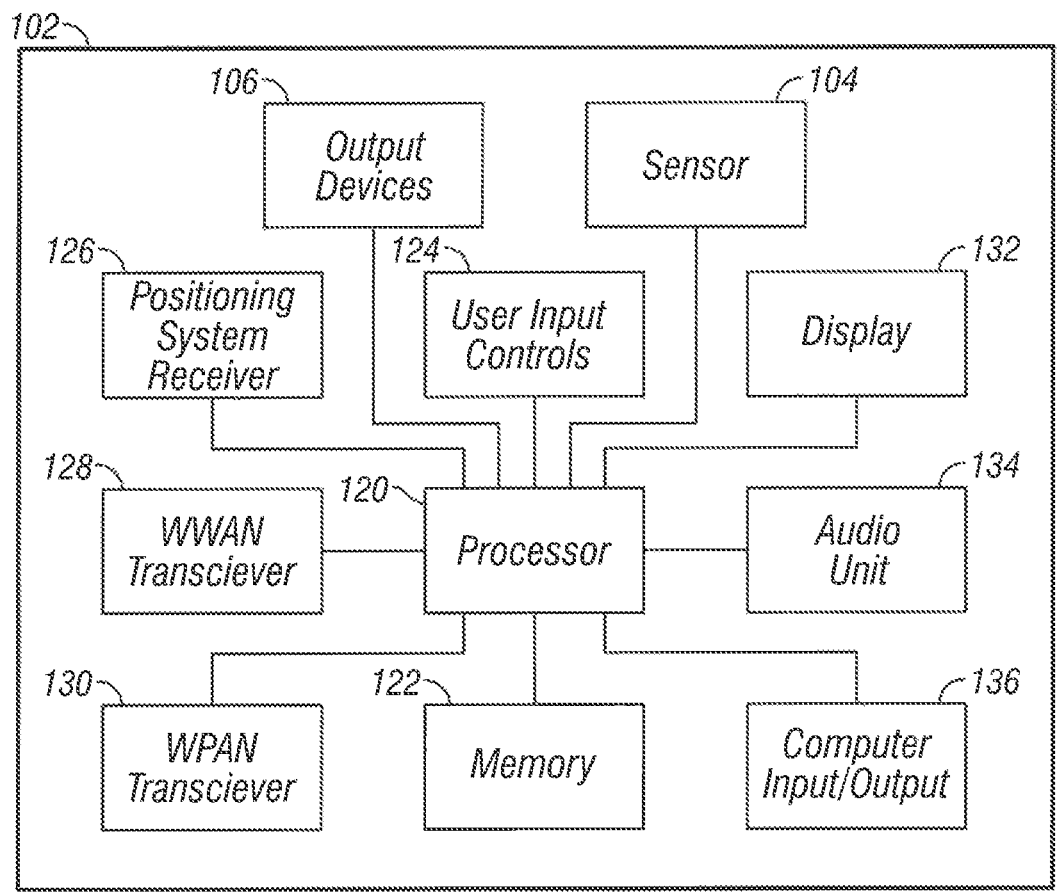
FIG. 3 is a block diagram of components of a portable fitness monitoring device according to an embodiment of the present invention.
Figure 4:
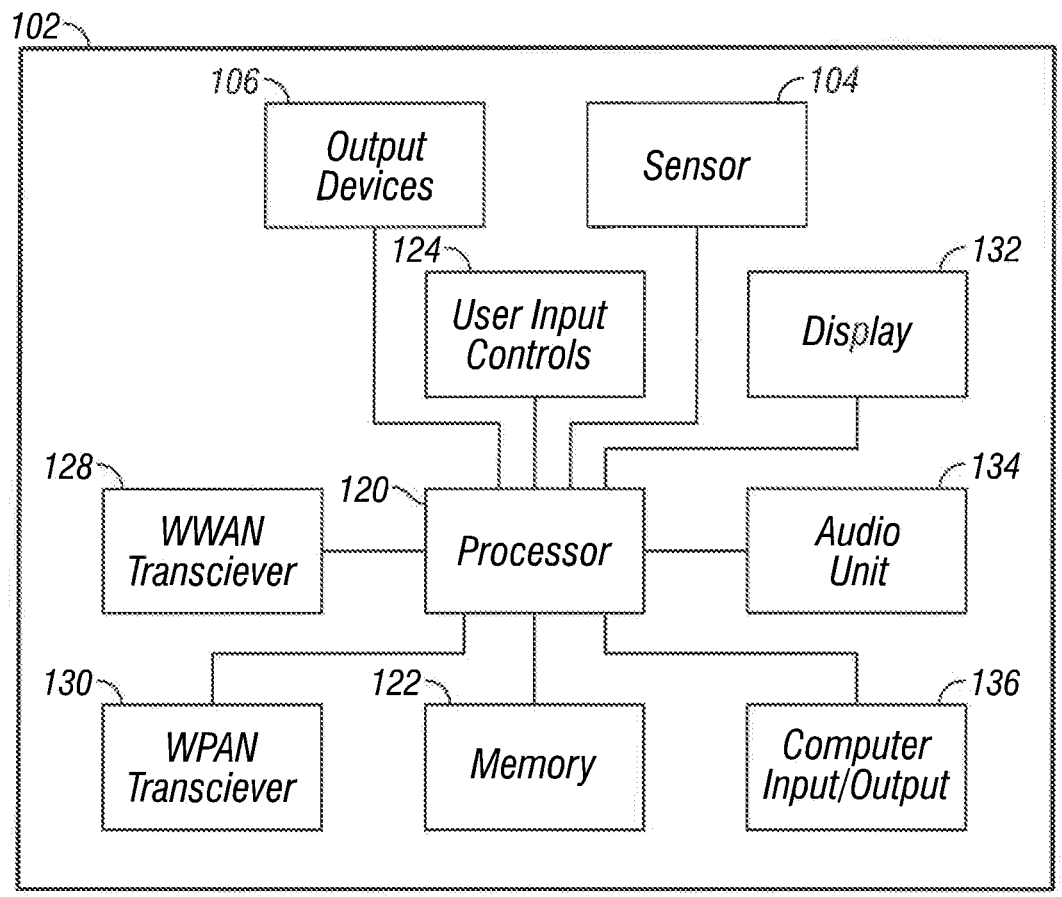
FIG. 4 is a block diagram of components of a portable fitness monitoring device according to an embodiment of the present invention.

FIG. 3 is a block diagram of exemplary components of a portable fitness monitoring device 102 according to an embodiment of the present invention. With reference to FIG. 3, the portable fitness monitoring device 102 may include a processor 120, a memory 122, user input controls 124, a positioning system receiver 126, a wireless wide area network (WWAN) transceiver 128, a wireless personal area network (WPAN) transceiver 130, a visual display 132, an audio unit 134, one or more sensors 104, output device 106, and a computer input/output 136. These components may be operatively connected to carry out the functionality of the portable fitness monitoring device 102. In other embodiments, one or more of these components may be omitted, or additional components may be included. For example, as shown in FIG. 4, the portable fitness monitoring device 102 may not include a positioning system receiver 126.

The processor 120 of the portable fitness processing device 102 may be adapted to implement application programs that are stored in the memory 122, such as those described in further detail below. For example, in one embodiment, the processor 120 may be adapted to execute a workout routine. In one embodiment, the processor 120 may also be capable of implementing analog or digital signal processing algorithms, such as, for example, those disclosed in U.S. patent application Ser. No. 11/892,023, titled "Sports electronic training system, and applications thereof," the disclosure of which has previously been incorporated herein in its entirety. The processor 120 may be operatively connected to the memory 122, the user input controls 124, the positioning system receiver 126, the WWAN transceiver 128, the WPAN transceiver 130, the visual display 132, the audio unit 134, the one or more sensors 104, the output device 106, and the computer input/output 136.

The memory 122 may be adapted to store application programs used to implement aspects of the functionality of the portable fitness monitoring system described herein. The memory 122 may also be adapted to store other data and information, as described in further detail below. For example, the memory 122 may be adapted to store recorded performance parameter information, workout routines and schedules, music tracks, map information, route data, and/or one or more playlists. The memory 122 may include both read only memory and random access memory.

The user input controls 124 may be used by the athlete 100 to interact with the portable fitness monitoring device 102. In an embodiment, user input controls 124 may include one or more physical input buttons, switches, and/or keys. In one embodiment, the user input controls 124 may include a track pad, scroll ball, and/or touch screen input controls (e.g. virtual input buttons, switches, and/or keys). In another embodiment, the user input controls 124 may include capacitance switches. In a further embodiment, the user input controls 124 may be voice-activated controls. The function of each of these user input controls 124 may be determined based on an operating mode of the portable fitness monitoring device 102.

In one embodiment, some or all of the user input controls 124 may not be integrally coupled to and/or included within the same housing as the portable fitness monitoring device 102 itself. For example, some or all of the user input controls 124 may be part of a separate visual display output device 106, such as a wristband or wristwatch-like device which may include a visual display and one or more buttons for input. Depending on how the portable fitness monitoring device 102 is supported by the athlete's 100 body during an activity, locating some or all of the user input controls 124 on a wristband may provide the athlete 100 with easier access to actuating the user input controls 124. Commands entered via the user input controls could be transmitted to the portable fitness monitoring device 102 wirelessly, as described in further detail elsewhere.

The visual display 132 may be a visual display output device 106 integrally coupled to the portable fitness monitoring device 102, as described above. The visual display 132 may be used to visually display information to the athlete 100. In an embodiment, the visual display screen 132 may be, for example, a liquid crystal display (LCD), a light-emitting diode (LED) display, a retina display, or a organic light-emitting diode (OLED) display. In another embodiment, a single display screen may include both the visual display 132 and the user input controls 124 in the form of touch screen input controls.

As described in further detail above with reference to FIG. 2, in one embodiment, one or more additional output devices 106 may not be integrally coupled to and/or included within the same housing as the portable fitness monitoring device 102 itself. For example, a separate visual display output device 106, such as those described above, may be in wired or wireless communication with the portable fitness monitoring device 102.

The audio unit 134 is used to process audio signals. The audio unit 134 may convert, for example, digital audio signals into amplified analog signals that can be used to drive an audible output device 106 (e.g. headphones or a speaker) in wired or wireless communication with the portable fitness monitoring device 102, as described above. The audio unit 134 may process a variety of audio signals such as, for example, signals associated with music tracks or verbal coaching and feedback provided to the athlete during a training activity.

The WPAN transceiver 130 may be capable of wireless communication with components of the portable fitness monitoring system supported by and/or in proximity to the athlete's 100 body. In one embodiment, the WPAN transceiver 130 is a low-power transceiver. The WPAN transceiver 130 may include an antenna, and may operate in an unlicensed frequency band, such as 2.4 GHz. In another embodiment, the WPAN transceiver may communicate using known wireless protocols, including, but not limited to, ANT and ANT+, by Dynastream Innovations, Bluetooth, Bluetooth LE, Bluetooth LET, WLAN, or BlueRobin. Other known wireless communication protocols may be used. In an embodiment, a WPAN receiver or a WPAN transmitter capable of only unidirectional communication may be used in place of the WPAN transceiver 130. In one embodiment, the WPAN transceiver may be an infrared transceiver.

In one embodiment, the WPAN transceiver 130 may communicate with sensors 104 of the portable fitness monitoring system. In another embodiment, the WPAN transceiver 130 may communicate with visual, audible, and/or tactile portable output devices 106. In a further embodiment, a plurality of WPAN transceivers 130 may be employed for communicating with various sensors 104 and/or output devices 106.

In a further embodiment of the present invention, the portable fitness monitoring device 102 may be capable of connecting to an adapter that may supplement or replace the functionality of the WPAN transceiver 130. Such an adapter may be necessary if, for example, a particular sensor 104 or output device 106 is not capable of communicating with the WPAN transceiver 130 (e.g. the sensor 104 or output device 106 uses a different wireless transmission protocol than the WPAN transceiver 130), or if the portable fitness monitoring device 102 does not include a WPAN transceiver 130. In one embodiment, the adapter may include a male component for physically engaging a female component of the portable fitness monitoring device 102, where the female component is in communication with the processor 120 of the portable fitness monitoring device 102. For example, in an embodiment, the adapter may include a jack capable of plugging into an audio output jack of the portable fitness monitoring device 102. Because a wide variety of portable fitness monitoring devices 102 include similar audio output jacks (e.g. a 3.5 mm TRS jacks), the same type of adapter may advantageously be used with a variety of devices. Alternatively, the adapter may include, for example, a USB, mini USB, SD card, or other suitable adapter that is capable of being plugged into a connection port of the portable fitness monitoring device 102, and may advantageously be used with a variety of devices.

In one embodiment, the adapter may be capable of receiving a data transmission encoded in accordance with a first data protocol and capable of sending a data transmission encoded in accordance with a second data protocol. Thus, the adapter may further facilitate the exchange of data between multiple components that otherwise may not be able to communicate in accordance with a single data protocol. In one embodiment, the adapter may be a dongle adapted for use with a personal computer, a mobile device, or a mobile phone, for example.

In contrast with the WPAN transceiver 130, the WWAN transceiver 128 may be a cellular transceiver that may be used to send and receive, for example, voice cellular telephone signals. The WWAN transceiver 128 may also be used to exchange information with a computer network such as, for example, the internet, as described in further detail below. The WWAN transceiver 128 may include an antenna.

The portable fitness monitoring device 102 may also include a satellite-based positioning system receiver 126, such as a GPS- or Galileo-compatible receiver, or a beacon based positioning system. Suitable positioning system receivers may include, for example, those disclosed in commonly owned U.S. patent application Ser. No. 10/759,289, titled "Location-aware fitness training device, methods, and program products that support real-time interactive communication and automated route generation," the disclosure of which is incorporated herein by reference in its entirety. In one embodiment, the positioning system receiver 126 may function as a sensor 104 integrally coupled to the portable fitness monitoring device 102, and may allow the portable fitness monitoring device 102 to detect information that may be used to measure and/or calculate GPS waypoints, time, location, distance traveled, speed, and/or calories.

The computer input/output 136 may be any input/output device or transceiver capable of wired or wireless communication with a personal computer 114. In one embodiment, the computer input/output 136 may be a USB port capable of receiving a USB hardwire cable for connecting the portable fitness monitoring device 102 to the personal computer 114. Alternatively, the computer input/output 136 may be an audio jack or a memory card slot, as described above, or a connection port. In some embodiments, a separate computer input/output 136 may not be necessary if the portable fitness monitoring device 102 and the computer 114 are capable of communicating wirelessly via, for example, the WPAN transceiver 130 or the WWAN transceiver 128.

Figure 5:
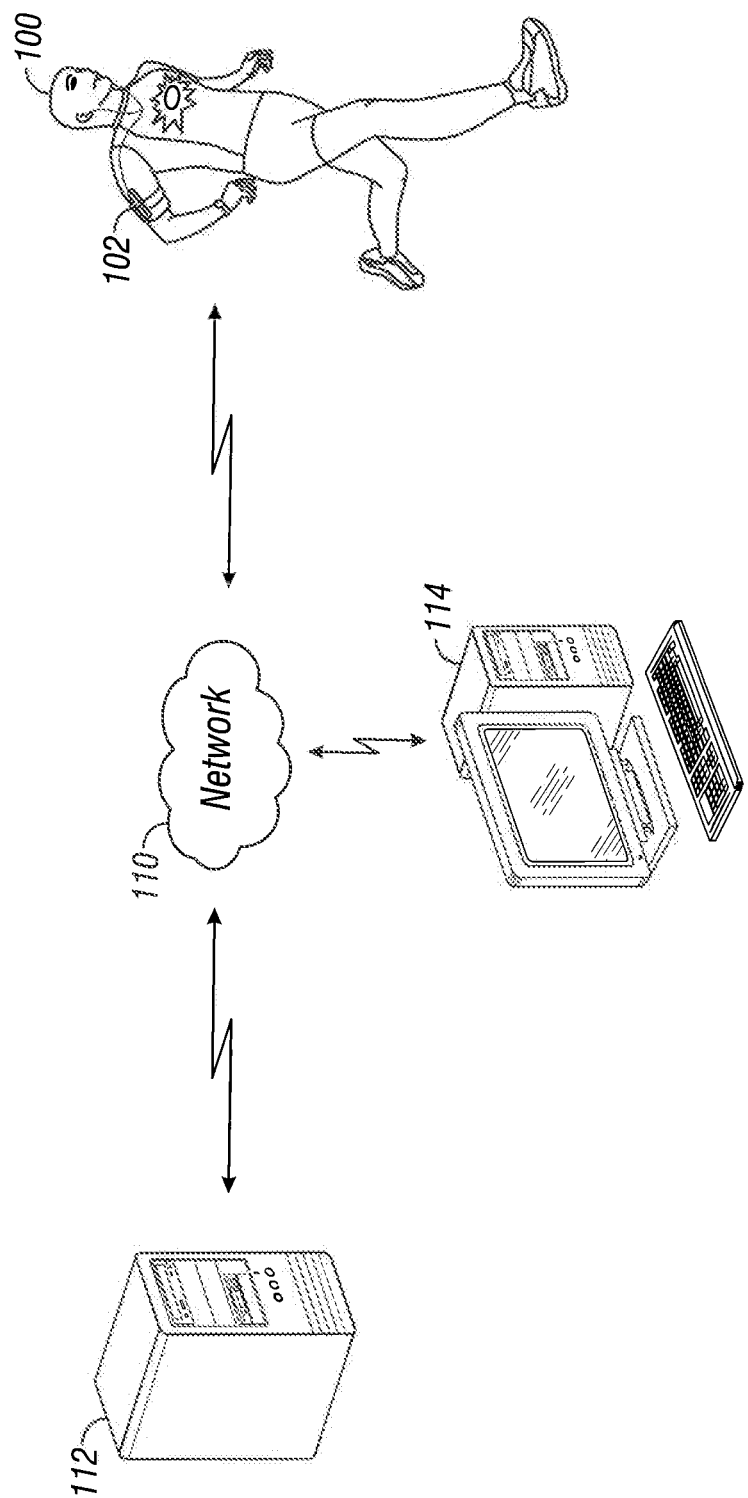
FIG. 5 is an illustration of a portable fitness monitoring device communicating with a server according to an embodiment of the present invention.

According to an embodiment of the present invention, information may be communicated between the portable fitness monitoring device 102 and one or more external elements. In addition, the external elements themselves may communicate between one another. As illustrated in FIG. 5, these external elements may include, for example, a network 110, a computer server system 112, and/or a personal computer 114.

In an embodiment, the network 110 may be the internet. The internet is a worldwide collection of servers, routers, switches and transmission lines that employ the Internet Protocol (TCP/IP) to communicate data. In an alternate embodiment, the network may be a private network or intranet. Other suitable communication networks may be used.

In one embodiment, a user (who may or may not be the athlete 100) stationed at the personal computer 114 located remotely from the server 112 may communicate with the server 112 via the network. For example, as explained in further detail below, the user may use a website provided by the server 112 to plan and schedule a prospective physical activity to be conducted by the athlete 100 using the portable fitness monitoring device 102. After the activity has been conducted, the user may also use the website provided by the server 112 to review and analyze performance information associated with the activity. Alternatively, an athlete-user 100 may access the website before, during, and after the activity directly from their portable fitness monitoring device 102. In one embodiment, the version of the website accessible from the athlete's portable fitness monitoring device may be simplified or otherwise modified to optimize it for display on a relatively small screen. For example, in one embodiment, planning and scheduling may be conducted through a mobile "app".

In another embodiment, the portable fitness monitoring device 102 may communicate wirelessly with server 112 via the network 110. Such communication may be achieved, for example, by way of the WWAN transceiver 128 of the portable fitness monitoring device 102 utilizing a wide area network. Alternatively, communication may be achieved by way of the WPAN transceiver 130.

For example, the portable fitness monitoring device 102 may communicate with a WWAN communications system such as that employed by mobile telephones. For example, a WWAN communication system may include a plurality of geographically distributed communication towers and base station systems. Communication towers may include one or more antennae supporting long range two-way radio frequency communication wireless devices, such as the portable fitness monitoring device 102. The radio frequency communication between antennae and the portable fitness monitoring device 102 may utilize radio frequency signals conforming to any known or future developed wireless protocol, for example, GSM, GPRS, EDGE, EV-DO, UMTS, LTE, CDMA, AMPS, IEEE 802.x (e.g., IEEE 802.16 (WiMAX)), etc. The information transmitted over-the-air by the base station systems and the cellular communication towers to and/or from the portable fitness monitoring device 102 may be further transmitted to or received from one or more additional circuit-switched or packet-switched communication networks, including, for example, the internet.

Wireless communication between the portable fitness monitoring device 102 and the server 112 via the network 110 may occur before, during, and/or after an athletic performance conducted using the portable fitness monitoring device 102, as explained in further detail below. Prior to the activity, the server 112 may send, for example, activity goal or route information to the portable fitness monitoring device 102. For example, the server 112 may send one or more workout routines to the portable fitness monitoring device 102. During the activity, the portable fitness monitoring device 102 may send, for example, real-time performance information to the server 112, and in response the server 112 may send, for example, real-time feedback or coaching to the portable fitness monitoring device 102. In one embodiment, this communication during the activity may occur as a result of and/or simultaneously with the execution of a workout routine by the portable fitness monitoring device 102. After the activity, the portable fitness monitoring device 102 may send, for example, complete activity performance information to the server 112, and in response the server 112 may send, for example, post-activity analysis to the portable fitness monitoring device 102.

Figure 6:
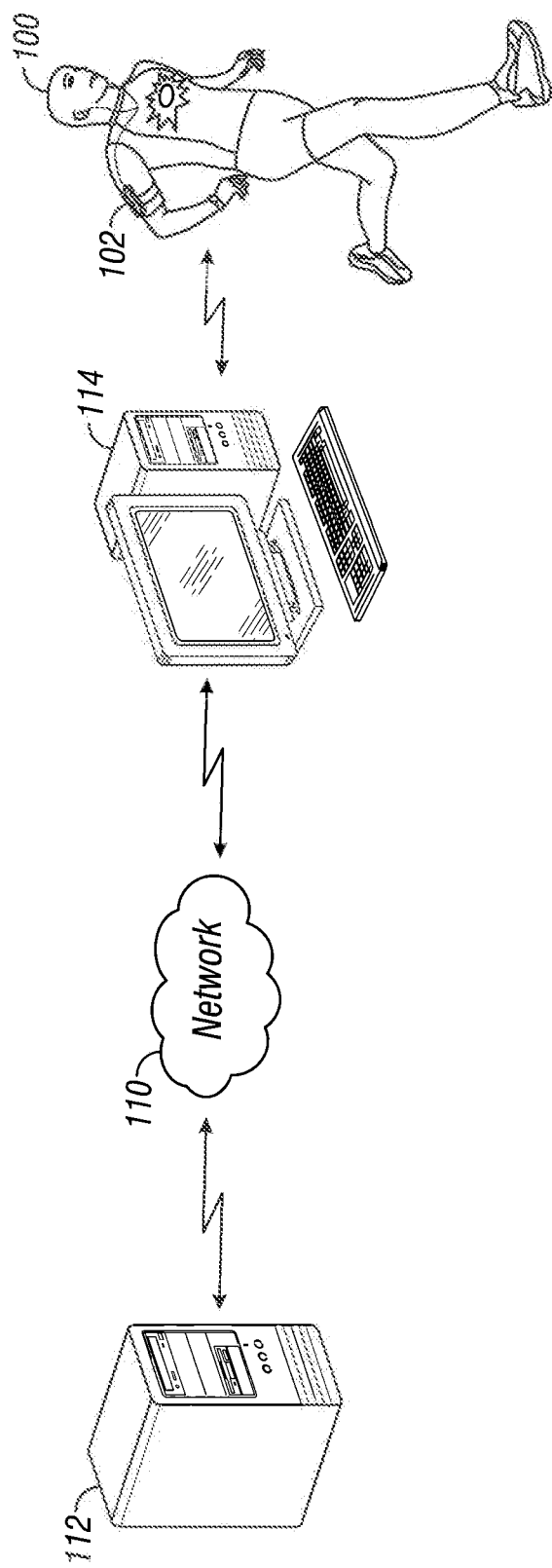
FIG. 6 is an illustration of a portable fitness monitoring device communicating with a server according to an embodiment of the present invention.

In another embodiment, as shown in FIG. 6, the portable fitness monitoring device 102 may communicate indirectly over the network 110 with the server 112 through the personal computer 114. Communication between the portable fitness monitoring device 102 and the personal computer 114 may be achieved, for example, using wired, WPAN, or WWAN communications. In one embodiment, as shown, for example, in FIG. 7B, a group of individuals having portable fitness monitoring devices 102 and one or more sensors 104 may communicate with a base station 116 that may be connected to the server 112 through a wired or wireless connection. The base station 116 may be a self-contained unit adapted to receive and transmit data to and from the portable fitness monitoring devices 102, the one or more sensors 104, and the server 112, and may be portable such that the base station may be proximate to an athletic activity (e.g., proximate a playing field). In one embodiment, a suitable base station 116 arrangement may include, for example, the base station and devices disclosed in commonly owned U.S. patent application Ser. No. 13/077,494, titled "Group Performance Monitoring System and Method," the disclosure of which is incorporated herein by reference in its entirety.

As will be appreciated by those of ordinary skill in the art, wired communication between the portable fitness monitoring device 102 and the personal computer 114 may be achieved, for example, by placing the portable fitness monitoring device 102 in a docking unit that is attached to the personal computer 114 using a communications wire plugged into a communications port of the personal computer 114.

In another embodiment, wired communication between the portable fitness monitoring device 102 and the personal computer 114 may be achieved, for example, by connecting a cable between the portable fitness monitoring device 102 and the computer 114. The computer input/output 136 of the portable fitness monitoring device 102 and a communications port of the computer 114 may include USB ports. The cable connecting the portable fitness monitoring device 102 and the computer 114 may be a USB cable with suitable USB plugs including, but not limited to, USB-A or USB-B regular, mini, or micro plugs. Alternatively, the cable may be a audio-jack-to-USB cable or other suitable communication cable.

Wired, WPAN, or WWAN communication between the portable fitness monitoring device 102 and the personal computer 114 may occur before and/or after an athletic performance is conducted using the portable fitness monitoring device 102 if the athlete 100 is in relatively close proximity to the personal computer 114, as explained in further detail below.

Figure 7A:
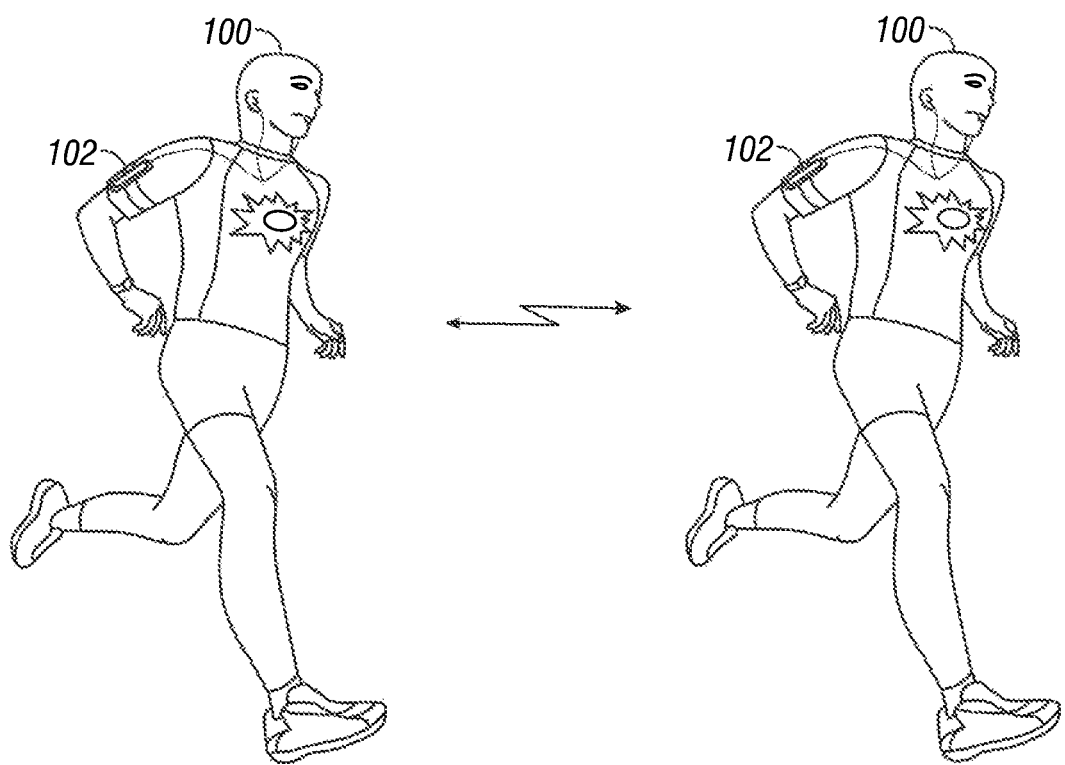
FIG. 7A is an illustration of one athlete's portable fitness monitoring device communicating with another athlete's portable fitness monitoring device according to an embodiment of the present invention.
Figure 7B:
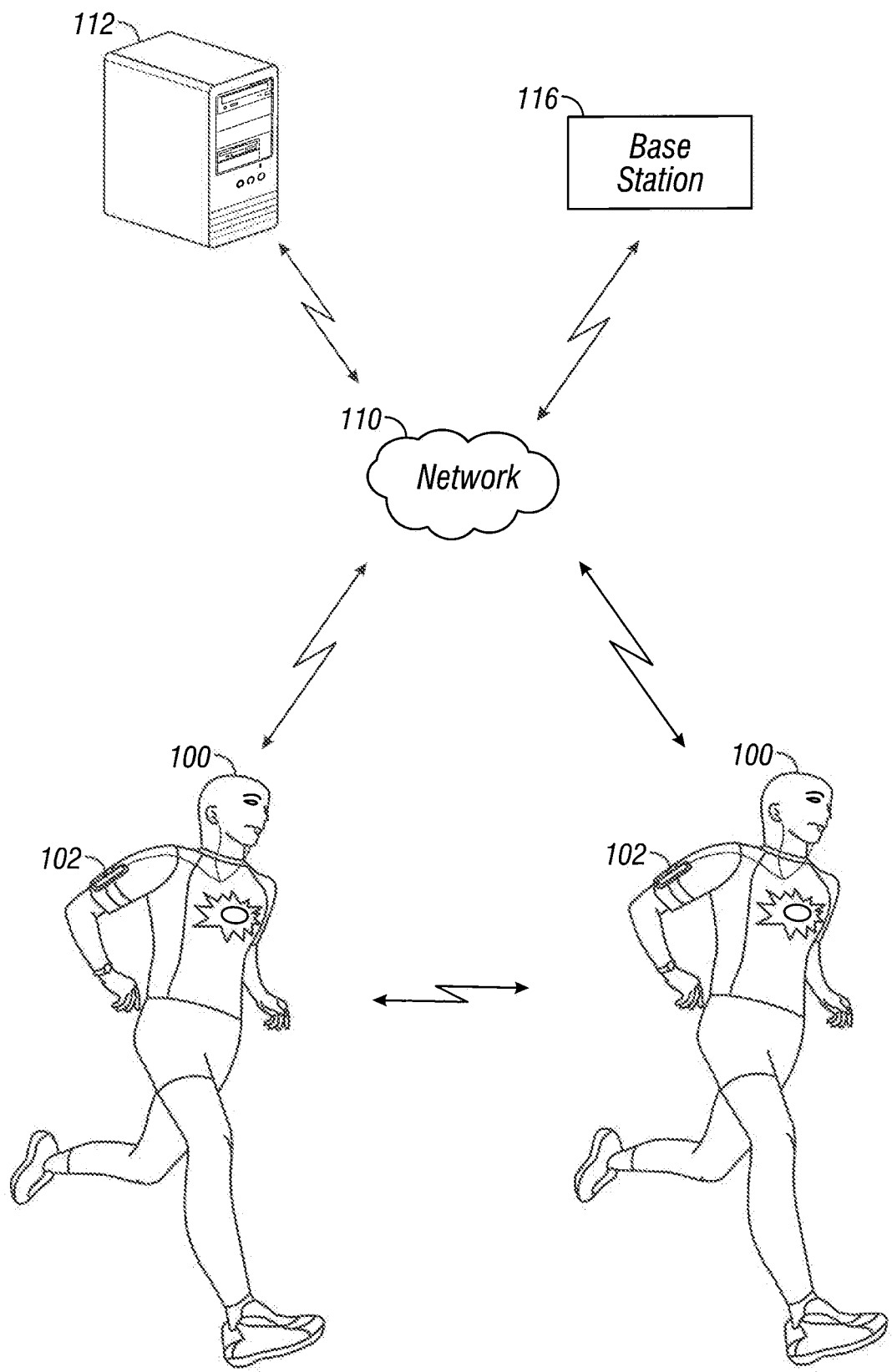
FIG. 7B is an illustration of a group of individuals with portable fitness monitoring devices communicating with a base station according to an embodiment of the present invention.

In one embodiment, as shown in FIG. 7A, one athlete's 100 portable fitness monitoring device 102 may be capable of communicating with another athlete's 100 portable fitness monitoring device 102. Communication may occur directly between the devices 102, or via a network 110. Such communication may occur wirelessly or via a hardwire connection, as explained above.

According to embodiments of the fitness monitoring methods of the present invention, a wide variety of information may be communicated between any of the personal fitness monitoring device 102, the personal computer 114, the network 110, and the server 112. Such information may include, for example, performance parameters, training advice, training plans, workout routines, calendar data, route information, music, videos, text, images, voice communications, settings, software, and firmware, as described in further detail below.

Figure 8:
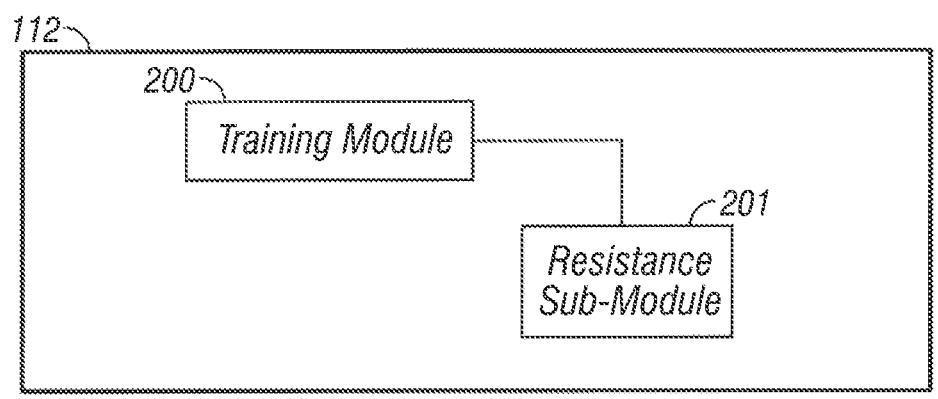
FIG. 8 is a block diagram of an exemplary software configuration of a server according to an embodiment of the present invention.
Figure 9:
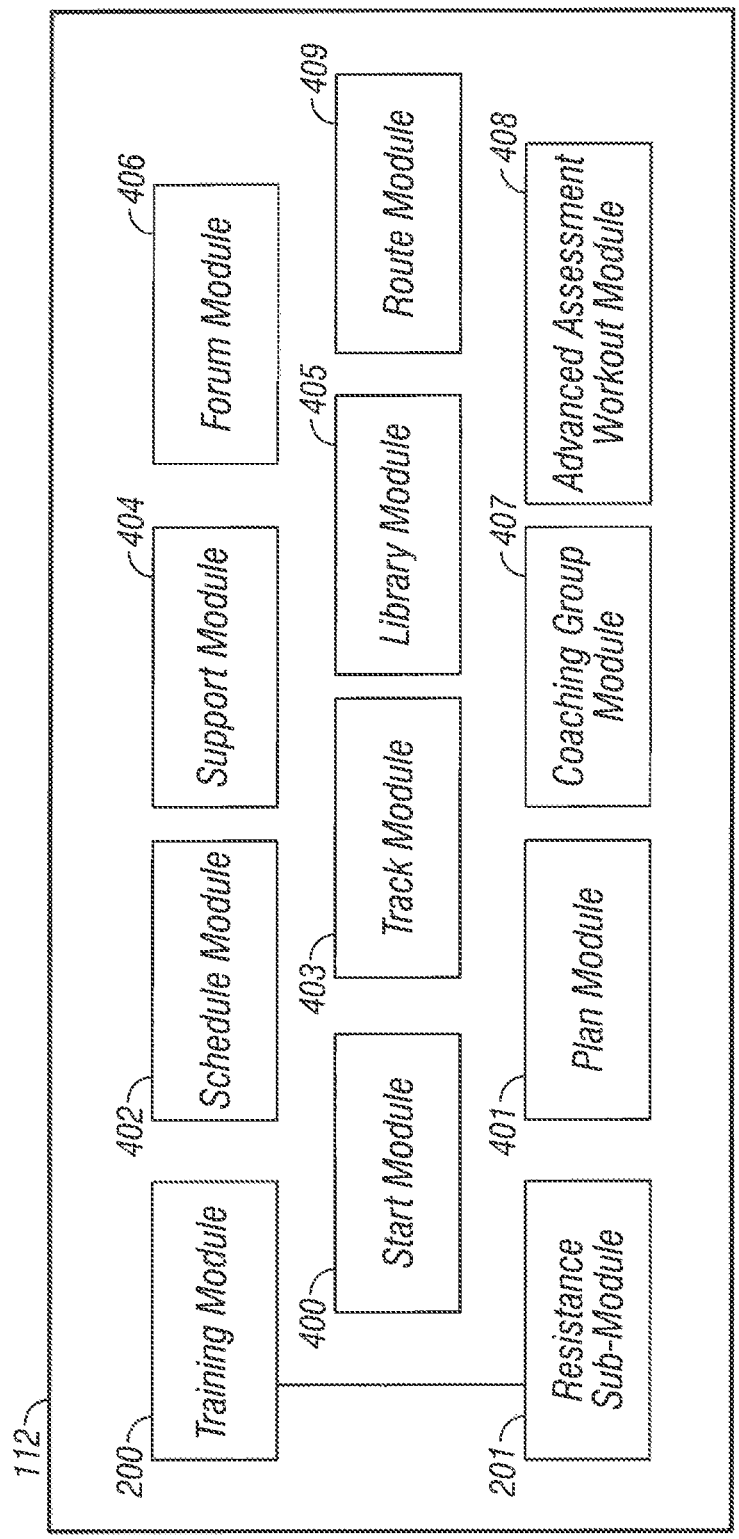
FIG. 9 is a block diagram of an exemplary software configuration of a server according to an embodiment of the present invention.

FIG. 8 is a diagram of an exemplary software configuration of the server 112. The application software of server 112 may include a number of different modules capable of providing fitness monitoring methods to athletes 100. In one embodiment of the present invention, the application software may include a training module 200. Training module 200 supports one or more graphical user interfaces (GUIs) capable of being presented to athletes 100 at one or more portable fitness monitoring devices 102 and/or users at remote personal computers 114. Embodiments of the present invention may further employ software modules described in commonly owned U.S. Patent Application Publication No. 2010/0292600, entitled "Program Products, Methods, and Systems for Providing Fitness Monitoring Services," the disclosure of which is incorporated by reference thereto in its entirety, in commonly owned U.S. patent application Ser. No. 12/468,025, entitled "Program Products, Methods, and Systems for Providing Fitness Monitoring Services," the disclosure of which is incorporated by reference thereto in its entirety, and in commonly owned U.S. patent application Ser. No. 12/836,421, entitled "Fitness Monitoring Methods, Systems, and Program Products, and Applications Thereof," the disclosure of which is incorporated by reference thereto in its entirety. For example, as shown in FIG. 9, in one embodiment training module 200 may be used in conjunction with or instead of one or more modules, including, but not limited to, a start module 400, a plan module 401, a schedule module 402, a track module 403, a support module 404, a library module 405, a forum module 406, a coaching group module 407, an advanced assessment module 408, and a route module 409. Those skilled in the art will appreciate that alternative or additional modules may be implemented within the server computer system 112 in order to provide or extend the described or additional functionality.

The server 112 may be, for example, a telecommunication server, a web server, or other similar types of database servers. In an embodiment, server 112 may have multiple processors and multiple shared or separate memory components such as, for example, one or more computing devices incorporated in a clustered computing environment or server farm. The computing process performed by the clustered computing environment, or server farm, can be carried out across multiple processors located at the same or different locations. In an embodiment, server 112 can be implemented on a single computing device.

As is known by those of skill in the art, a GUI may use a combination of technologies and devices to provide a platform that the athlete 100 or other user can interact with via the portable fitness monitoring device 102 or the personal computer 114. A GUI may offer, for example, graphical elements, visual indicators, and/or text to represent information and actions available to the athlete 100 or other user. Graphical elements may include, for example, windows, menus, radio buttons, check boxes, and/or icons. The athlete 100 or other user may use a physical input device, such as a mouse, track pad, and/or scroll ball to control the position of a cursor on their portable fitness monitoring device 102 or personal computer 114 screen. Alternatively, the athlete 100 or other user may use a touch screen, with or without a stylus, to interact directly with what is displayed (rather than indirectly via a cursor). Various touch screens such as, for example, resistive or capacitive touch screens, may be employed.

Those skilled in the art will appreciate that alternative or additional modules and sub-modules may be implemented within the server 112 in order to provide or extend the described or additional functionalities. For example, the software configuration of server 112 may include an operating system, which may be one of the commercially available operating systems such as, for example, Windows, UNIX, LINUX, Mac OSX, or AIX. The operating system may also have an associated application programming interface through which middleware and application programs may access the services of the operating system. In addition, a hypertext transport protocol (HTTP) server may run on top of the operating system. As is well known in the art, HTTP server may communicate data over the internet using HTTP.

As illustrated herein, training module 200 of the fitness monitoring methods of the present invention may support GUIs through which an athlete 100 or other user can interact with the fitness monitoring methods using the portable fitness monitoring device 102 and/or the personal computer 114. As will be appreciated by those of skill in the art, in one embodiment the GUIs may appear as web pages provided by the server 112 via a website that may be accessible to the athlete 100 or other user over the internet 110 using a web browser on their portable fitness monitoring device 102 or their personal computer 114. In other embodiments, the GUIs may be generated by a processor based only on information stored on the portable fitness monitoring device 102 or the personal computer 114, a CD-ROM, a memory card or other removable media, a mobile phone, or other computer readable media accessible locally. In embodiments of the present invention, athletes 100 or other users can, among other things, use data generated from past performances to gauge improvement, set goals for the future, share performance data with others, and/receive assistance in planning exercises at intensities appropriate for the athlete's 100 current fitness level and goals.

In an embodiment, the athlete 100 may be able to download mobile applications to portable fitness monitoring device 102, such as a mobile phone or a tablet computer, that are capable of presenting GUIs similar to those illustrated herein, from server 112. Accordingly, the athlete 100 may be able to interact with the server 112, access their account, and perform many of the other planning, tracking, and other functions described herein from a mobile device.

Training module 200 may be accessed by the user, as variously described above, and may be employed to schedule one or more training activities based on a desired training category. In this manner, the user may use the training module 200 to plan and schedule one or more training activities that are specifically geared toward a desired objective, e.g., training category. The training activities may include a single, one-time training activity (e.g., 10 knee bends or 10 minutes of yoga), or may include a plurality of activities. As will be discussed in detail below, the training activities may be part of cardio based workouts and/or non-cardio based workouts, such as, for example strength based workouts, depending on the desired training category. Cardio based workouts may include one or more training activities that include a continuous aerobic exercise. In one embodiment, cardio based workouts may include a cardio goal, including, but not limited to, a heart rate goal, speed goal, and/or a pace goal. Non-cardio based workouts may include one or more movement-based training activities that are generally non-aerobic. As discussed below, non-cardio based workouts may include a particular resistance goal including a load, time, and/or repetition goal, or may not include one or any of these goals. For example, a load goal may comprise a weight goal (e.g., 100 pounds); a repetition goal may comprise a number of times for completing a movement (e.g., 10 repetitions of a bench press); and a time goal may comprise a length of time for performing a number of movements.

In one embodiment, the training categories 202 may correspond to one or more particular sports. For example, a user who wishes to train for soccer may select a soccer training category which would facilitate scheduling of training activities, including a combination of cardio based training activities and non-cardio based activities (e.g., a strength based activity), which may prepare the user for the rigors of soccer (e.g., stamina and leg strength). Training categories 202 also may be directed to broad fitness categories, such as, for example, losing weight, staying fit, running faster, cycling faster, and other suitable categories.

Figure 10:
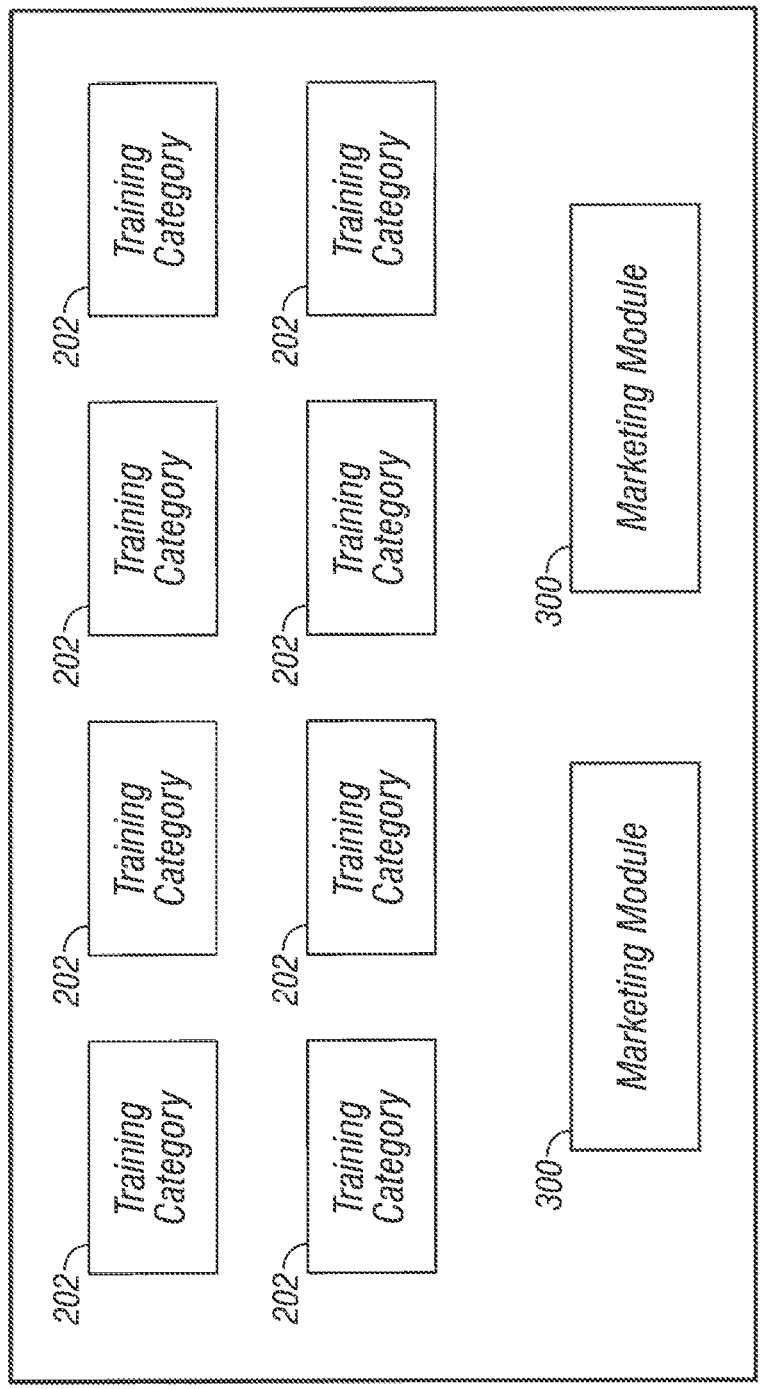
FIG. 10 is an exemplary GUI window for selecting a training category according to an embodiment of the present invention.
Figure 11:
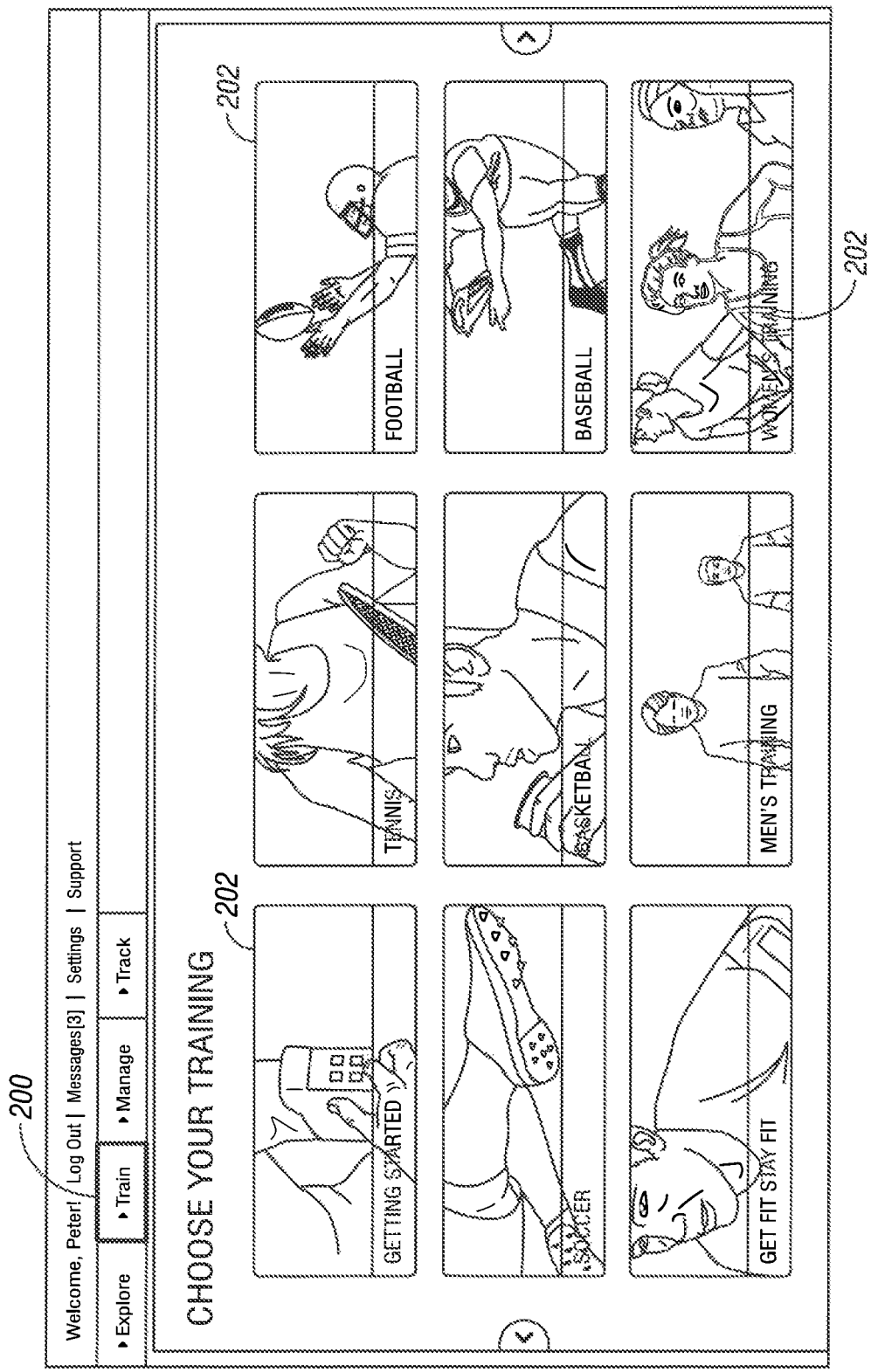
FIG. 11 is an exemplary GUI window for selecting a training category according to an embodiment of the present invention.

FIGS. 10 and 11 are exemplary GUI windows according to embodiments of the present invention that may be displayed by the training module 200. From the main training module page, the user (who may or may not be the athlete 100) may be able to select from one of a plurality of icons corresponding to training categories 202. The training categories 202 may include, but are not limited to, basketball, tennis, football, soccer, recreational running, walking, skating, swimming, performing aerobic exercises, weight lifting, general fitness, baseball, boxing, hockey, field hockey, rugby, crew/rowing, race running, sprint running, cycling, lacrosse, golf, martial arts, gymnastics, wrestling, yoga, skiing, paddle boarding, and snowboarding. One or more marketing modules 300 may be included in any GUI window, such as, for example, advertisements, or links to marketing related content.

Figure 12:
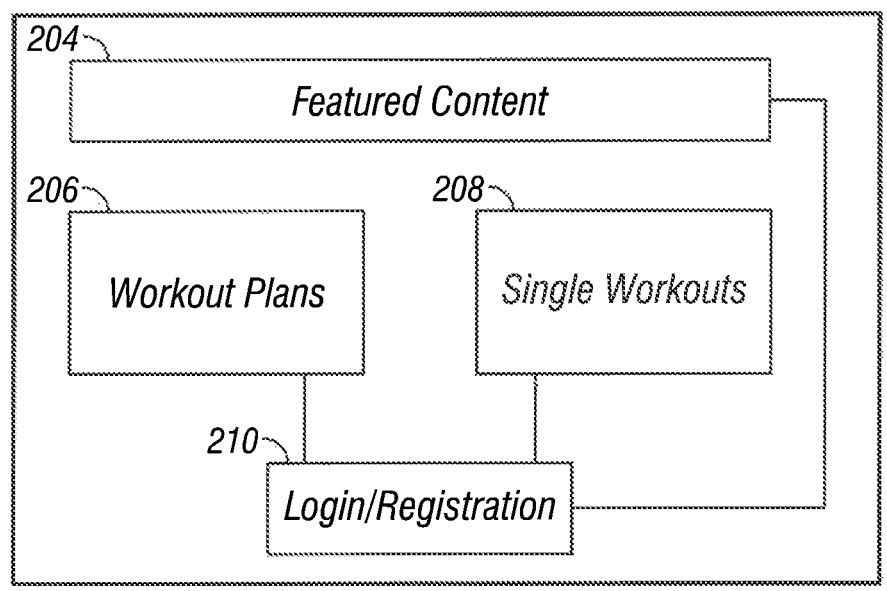
FIG. 12 is an exemplary GUI window for selecting a workout according to an embodiment of the present invention.
Figure 13:
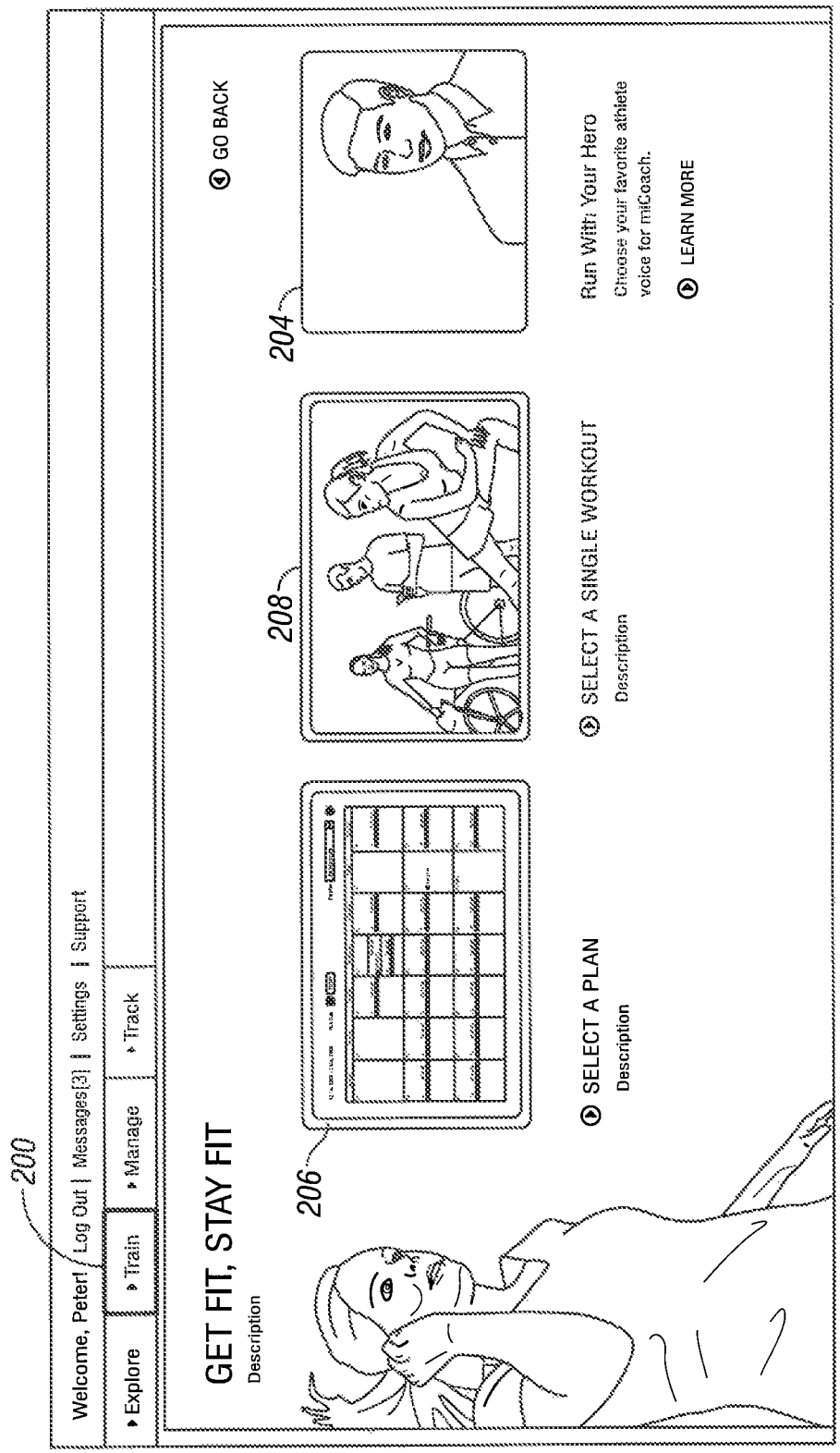
FIG. 13 is an exemplary GUI window for selecting a workout according to an embodiment of the present invention.

FIGS. 12 and 13 are exemplary GUI windows according to embodiments of the present invention that may be displayed by the training module 200 after the user has selected a particular training category 202. In one embodiment, the user may select from one of a plurality of icons corresponding to featured content 204, workout plans 206, and single workouts 208 which correspond to the selected training category 202. The featured content 204 may include a featured highlight relating to the selected training category 202. For example, the featured highlight may include a motivational video relating to soccer and the types of workouts that may be included in the training category. In one embodiment, the featured content 204 may include featured workout plans and featured single workouts, which may include a plurality of training activities for scheduling. In one embodiment, featured content 204 may include a feature such as a list of voices that may be selected as a coaching voice (e.g., famous athlete or drill sergeant).

Figure 14:
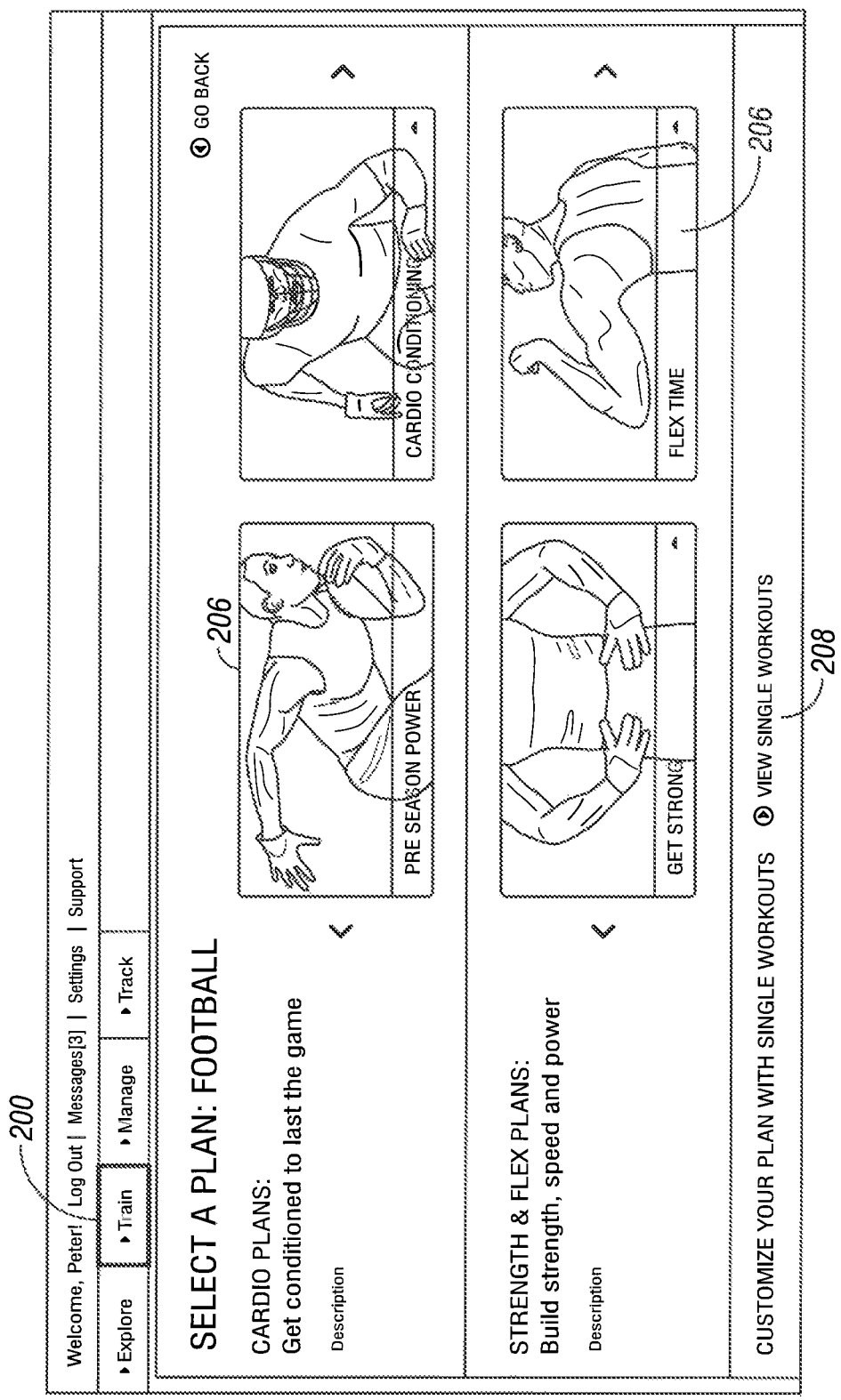
FIG. 14 is an exemplary GUI window for selecting a workout according to an embodiment of the present invention.

FIG. 14 is an exemplary GUI window according to an embodiment of the present invention that may be displayed by the training module 200 after the user has selected a particular training category 202. With reference to FIG. 14, in one embodiment a user may select a cardio based workout plan 206 and/or a non-cardio based workout plan 206 (e.g., a strength and flexibility plan), which corresponds to the selected training category 202. Each workout plan 206 may include one or more cardio based and/or one or more non-cardio based training activities. As shown, the user may select from a plurality of workout plans 206 that correspond to the selected training category 202. In one embodiment of the present invention, the training module 200 may enable the user to select workout plan icons associated with various workout plan sub-modules, such as, for example, a Pre-Season Power cardio plan, a Cardio Conditioning plan, a Get Strong plan, and a Flex Time plan. Other workout plan sub-modules corresponding to a selected training category 202, including, but not limited to, a Learn to Run sub-module, a Be Fit sub-module, a Run a Race sub-module, a De-Stress sub-module, a Lose Weight sub-module, and a Finish Faster sub-module may be included. Workout plan sub-modules of embodiments of the present invention may include features such as, for example, those disclosed in commonly owned U.S. patent application Ser. No. 12/836,421, entitled "Fitness Monitoring Methods, Systems, and Program Products, and Applications Thereof," the disclosure of which has been incorporated by reference thereto in its entirety. As shown in FIG. 14, the GUI may display an icon associated with a particular workout plan 206 and provide a brief description including, for example, a selection of intensity levels. A user may select a single workout 208 to add a single workout to the selected workout plan 206, or to just schedule an individual workout.

Figure 15:
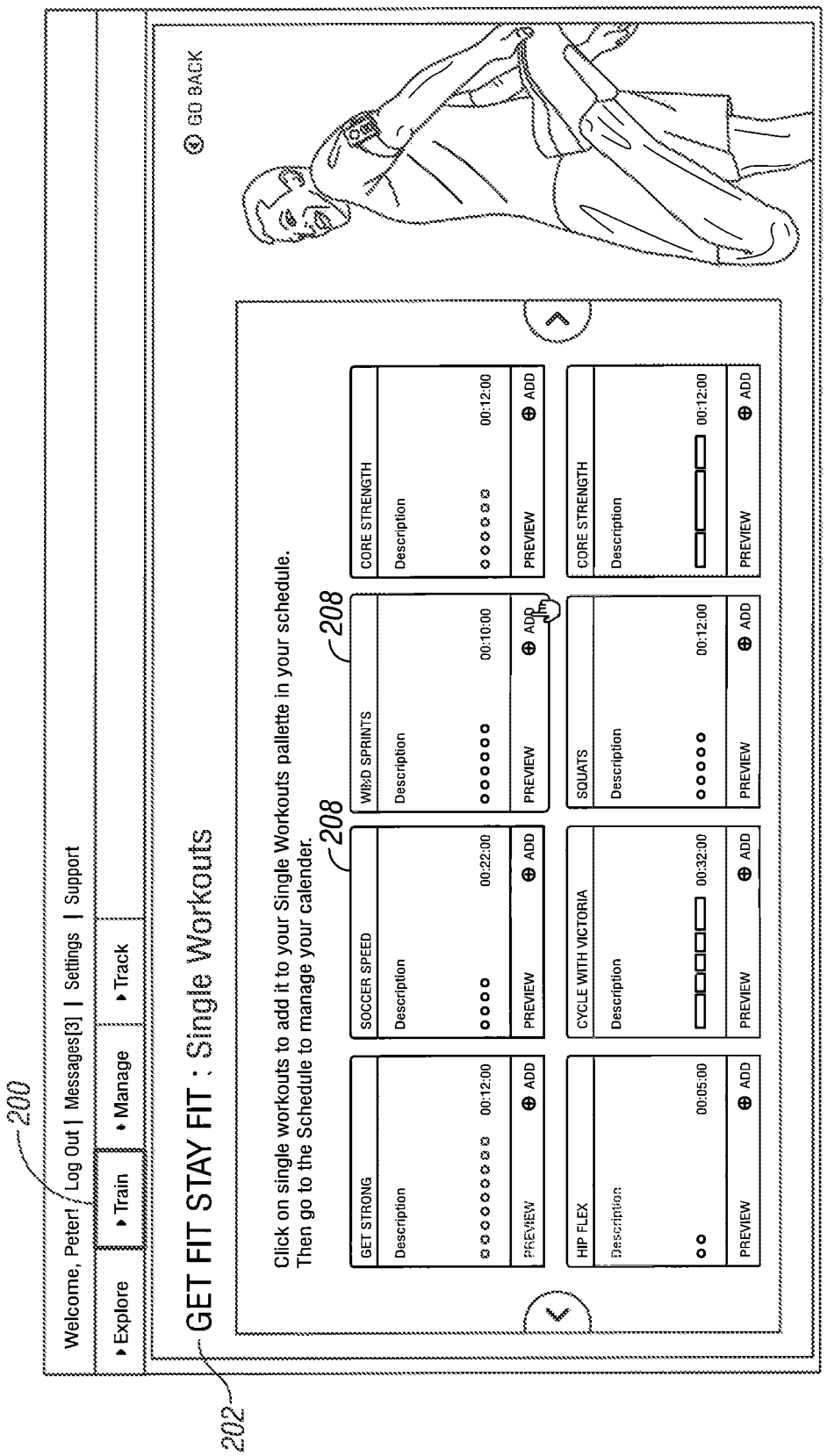
FIG. 15 is an exemplary GUI window for selecting a workout according to an embodiment of the present invention.

FIG. 15 is an exemplary GUI window according to an embodiment of the present invention that may be displayed by the training module 200 after the user has selected a particular training category 202. The user may select from a plurality of single workouts 208 that correspond to the selected training category 202. Each workout 208 may include a training activity tailored to the particular objective of the training category 202, and may include cardio based and/or non-cardio based training activities. In one embodiment of the present invention, the training module 200 may enable the user to select one or more single workout icons associated with various single workout sub-modules, such as, for example, Get Strong, Soccer Speed, Wind Sprints, Core Strength, Hip Flex, Cycle with Victoria, Squats, and Zone Cycling 2. Other single workout sub-modules, including, but not limited to, Calf Strength 1, Calf Strength 2, Ankle Recovery 1, Ankle Recovery 2, Hip Recovery 1, Hip Recovery 2, Shin Splint Recovery, and Leg Strength may be included. As shown in FIG. 15, the GUI may display an icon associated with a particular workout 208 and provide a brief description including, for example, workout duration and the zone or intensity information for zone based workouts.

Figure 16:
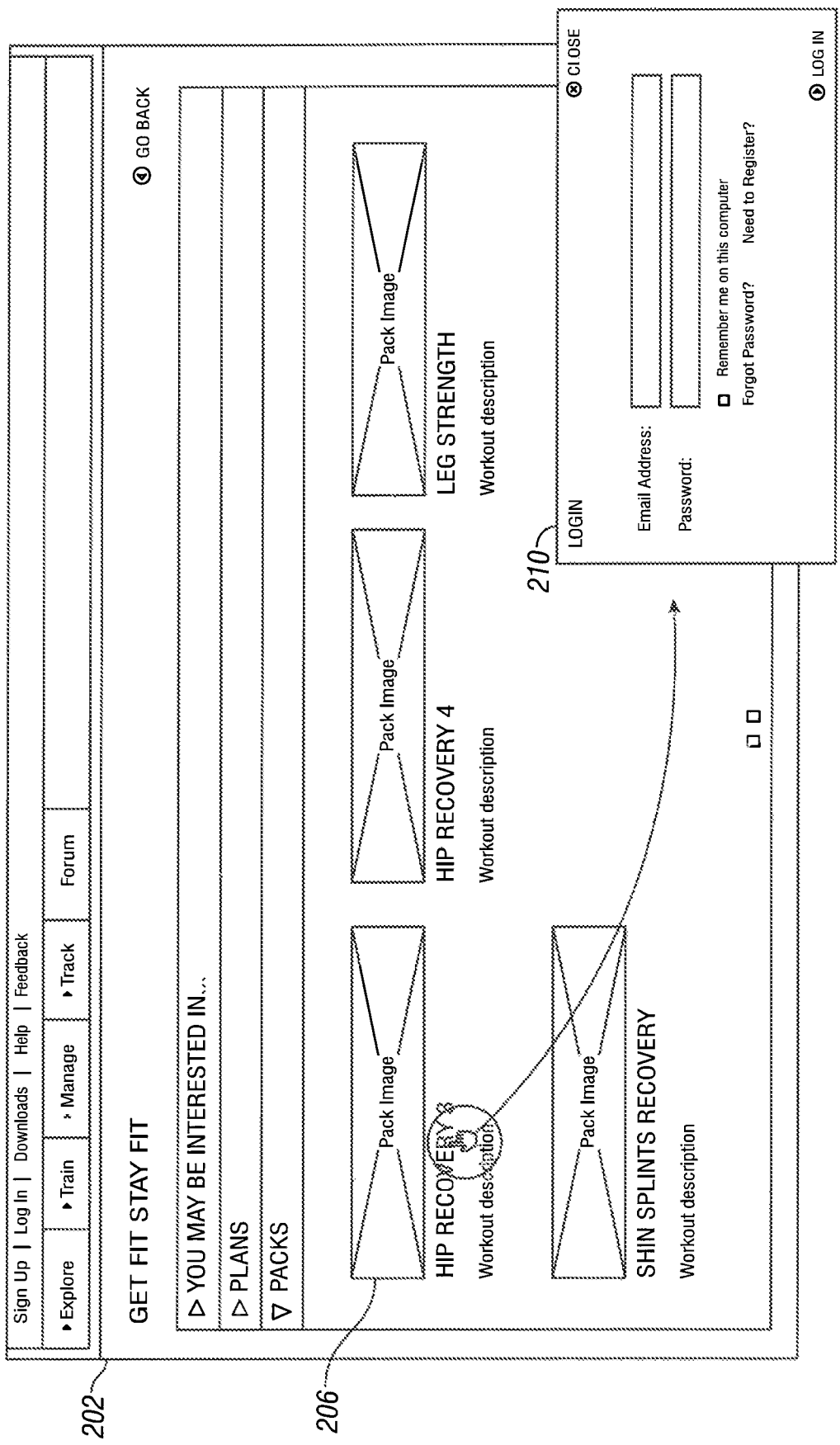
FIG. 16 is an exemplary GUI window according to an embodiment of the present invention.
Figure 17:
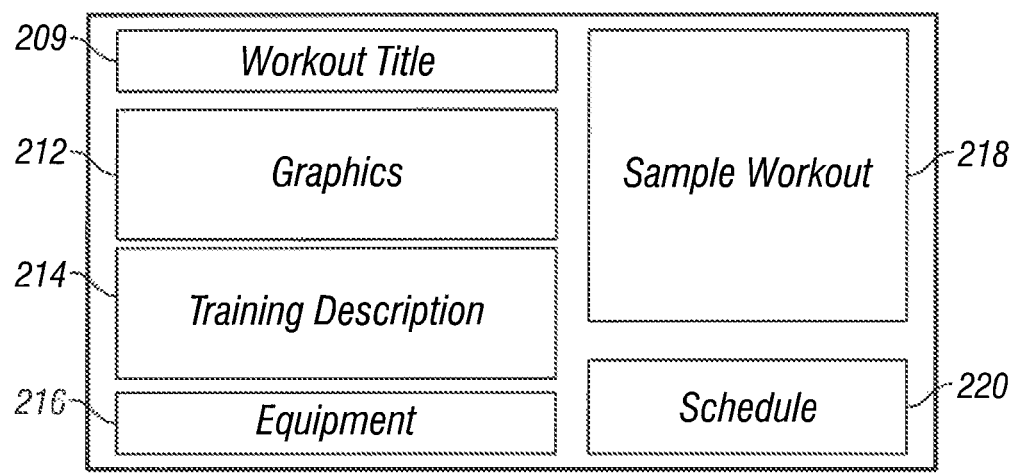
FIG. 17 is an exemplary GUI window including an exemplary workout according to an embodiment of the present invention.

In one embodiment, as shown, for example, in FIGS. 12 and 16, after the user has selected a desired workout plan and/or single workout, a login or start module may present the user with a login wizard 210 if the user is not otherwise logged in. In order to access the features of embodiments of the present invention prior to engaging in a physical activity, a user stationed at the remote personal computer 114 or at portable fitness monitoring device 102 may login to the server 112 via the internet 110. As is well known to those skilled in the art, the login process typically includes the entry by the remote user of a login ID and password or other authentication information to the server 112, which then authenticates the identity of the user by reference to a user database or the like. Embodiments of the fitness monitoring methods of the present invention may be offered to a plurality of athletes 100 or other users forming a user community, may be restricted to users that have been issued login IDs and passwords for accessing the server 112, and/or may further be offered in exchange for a subscription fee. If the user has not previously logged in or does not have login information, the user may register for a user account to the fitness monitoring methods from the login wizard 210.

FIGS. 17 through 21 are exemplary GUI windows according to embodiments of the present invention that may be displayed by the training module 200 after the user has selected a particular workout plan or single workout based on the selected training category 202. In one embodiment, the GUI window may provide workout details including the workout title 209 of the selected workout plan 206 or single workout 208, graphics 212 representative of the workout, a workout description 214, required equipment 216, and a sample workout 218.

Figure 18:
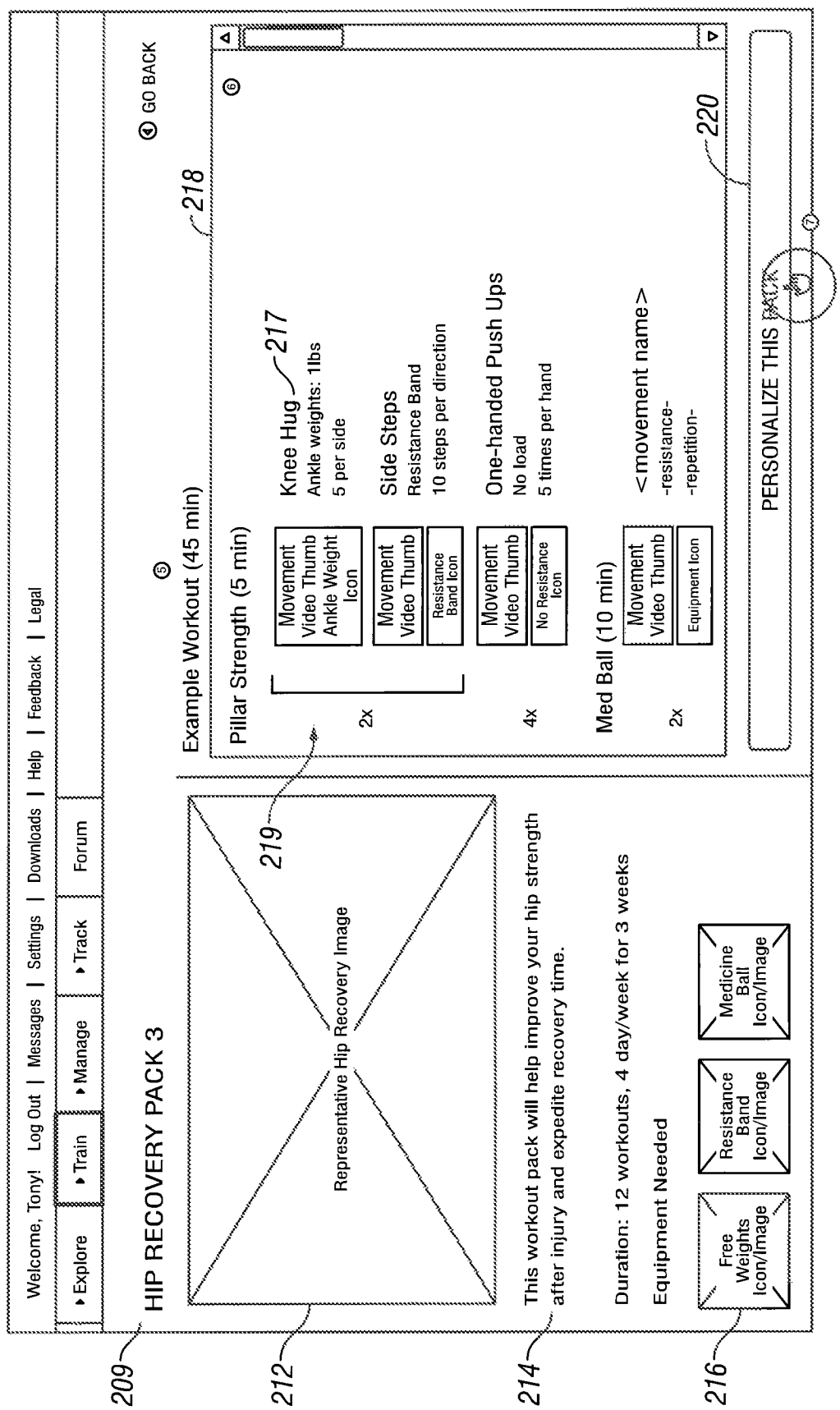
FIG. 18 is an exemplary GUI window including an exemplary workout according to an embodiment of the present invention.
Figure 19:
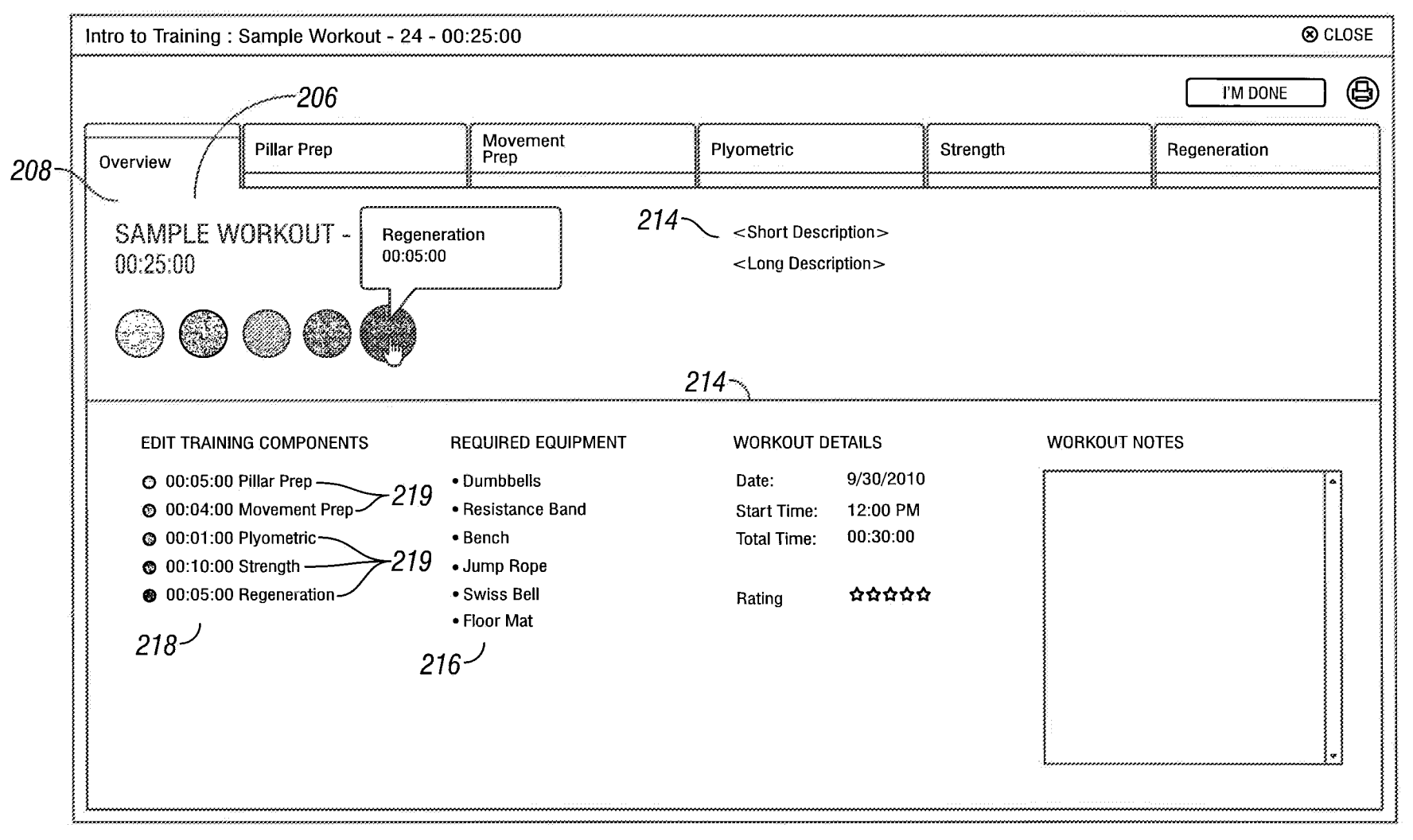

As shown, for example, in FIGS. 18 and 19, in one embodiment, the workout description 214 may include a description of the exercises included in the workout plan or single workout, the muscle groups that may be implicated or the general benefit of the exercises (e.g., "strength, "regeneration," etc.), the number of training activities in the workout plan, and the general schedule timing of the prospective training activities. For example, a workout plan may be described as helping improve hip strength after injury and expedite recovery time, and the schedule timing may include twelve (12) workouts, to be executed four (4) days per week for three (3) weeks. The required equipment 216 may provide graphical or textual information regarding the equipment required to complete one or more of the training activities. For example, for a non-cardio based training activity, the required equipment may include, but is not limited to, resistance equipment (e.g., dumb-bells, barbells, plates, resistance bands, a cable machine, a fixed weight or resistance machine, free weights, and a medicine ball), preparation equipment (e.g., bench, stability ball, pull-up bar, slides, towel, ankle straps, floor mat, cable handles, triceps rope, and step box), field equipment (hurdles, and cones), regeneration equipment (e.g., tennis ball, double tennis ball, foam roll, and stretch rope), and other suitable exercise equipment or combinations thereof.

Figure 21:
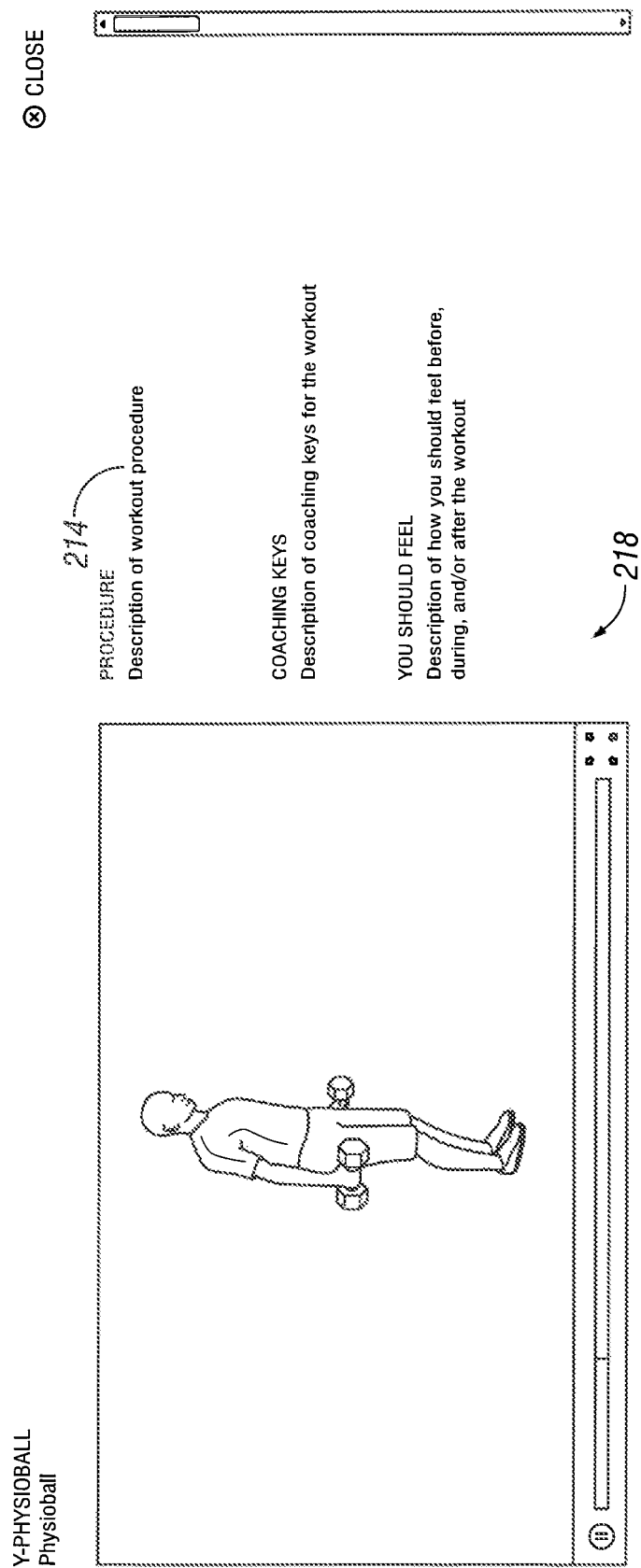
FIG. 21 is an exemplary GUI window according to an embodiment of the present invention.

In one embodiment, as shown, for example, in FIGS. 18, 19, and 20, training module 200 may further present a sample workout or training activity 218 that may be included in the selected workout plan or single workout based on the selected training category 202. The sample workout 218 may include a description of the individual body movements associated with the workout. The description may include a body movement name (e.g., Knee Hug, Pull Up, Bench Press, etc.), the equipment required for this particular body movement (e.g., Ankle weights: 1 lbs, Pullup Bar, Free Weight, etc.), and the number of repetitions required (e.g., 5 per side). In one embodiment, the description may further include a video associated with the workout or the individual body movement that may illustrate proper execution of the activity. The video may be accessed and viewed by the user before, during, and/or after execution of the workout to provide coaching instructions. For example, in one embodiment, the athlete 100 may access and view the video during the activity by using the portable fitness monitoring device 102 and/or the personal computer 114. In one embodiment, as shown in FIG. 21, the video may include a "virtual" performer that matches the gender of the user based on the user's account settings. The virtual performer may be dressed based on the selected training category 202 or specific training activity being performed. For example, in one embodiment, the virtual performer may be dressed in soccer apparel. In an embodiment, the virtual performer may be an "avatar" created by the user, and may also be used in conjunction with a video game, such as, for example, console gaming system 2000 described herein. In other embodiments, a textual description and/or audible narration of the activity may similarly be provided. For example the user may download an instructional description of the training activity and representative exercise drawings for viewing on the fitness monitoring device 102. In one embodiment, the user may print a description and representative exercise drawings for use during completion of the training activity.

The sample workout 218 may further include the recommended time required for each body movement and the number of repetitions for each. Upon selection of the desired workout plan, or individual training activity, the user may proceed to scheduling of the training activities via a "workout setup," as discussed in detail below, by manipulating a schedule button 220.

In one embodiment, a selected training activity may include a non-cardio based training activity and may require execution of a plurality of body movements. A non-cardio based training activity may be designed to address the strength and/or flexibility of a particular muscle or muscle group. In one embodiment, a workout or training activity may include one or more body movement circuits 217, which are a grouping of body movements performed in sequence that are repeated one to many times. With reference to FIGS. 18 and 20, a plurality of body movement circuits 217 may be grouped to comprise a workout component 219. For example, with reference to FIG. 18, a body movement circuit 217 may comprise a set of knee hugs, side step, or one-handed pushups. A plurality of body movement circuits 217—e.g., knee hugs and side steps—may be grouped as a training component 219 (e.g., Pillar Prep, Movement Prep, Plyometric, Strength, and Regeneration). In one embodiment, as shown in FIG. 19, for example, a visual representation of the intensity of the workout or each training component 219 may be provided. The visual representation may include a different color for a different intensity level, for example.

In one embodiment, the training activity may further include a corresponding load resistance depending on the needs, goals, and/or other constraints of the athlete 100. The load resistance may include one or more of an associated time requirement, resistance (e.g., weight) requirement, repetition requirement, or any combination of these requirements. As shown in FIG. 20, for example, in one embodiment, a bench press exercise may include three sets of movement, with 15 repetitions. The first two sets may be scheduled for completion with 10 lbs. of weight, and the third set may be scheduled for completion with 5 lbs. of weight. In one embodiment, the non-cardio based training activity may not include any associated time, resistance or repetition requirement.

Figure 22:
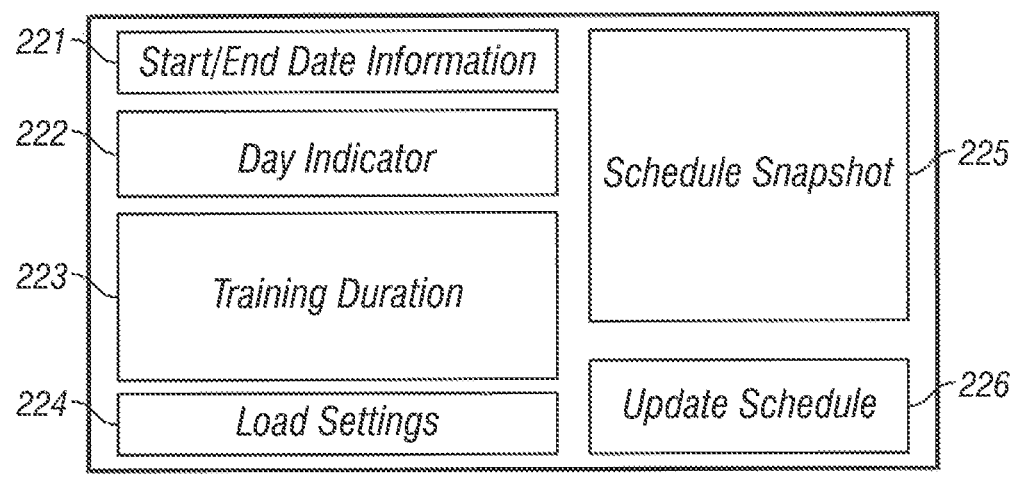
FIG. 22 is an exemplary GUI window for generating a workout schedule according to an embodiment of the present invention.
Figure 23:
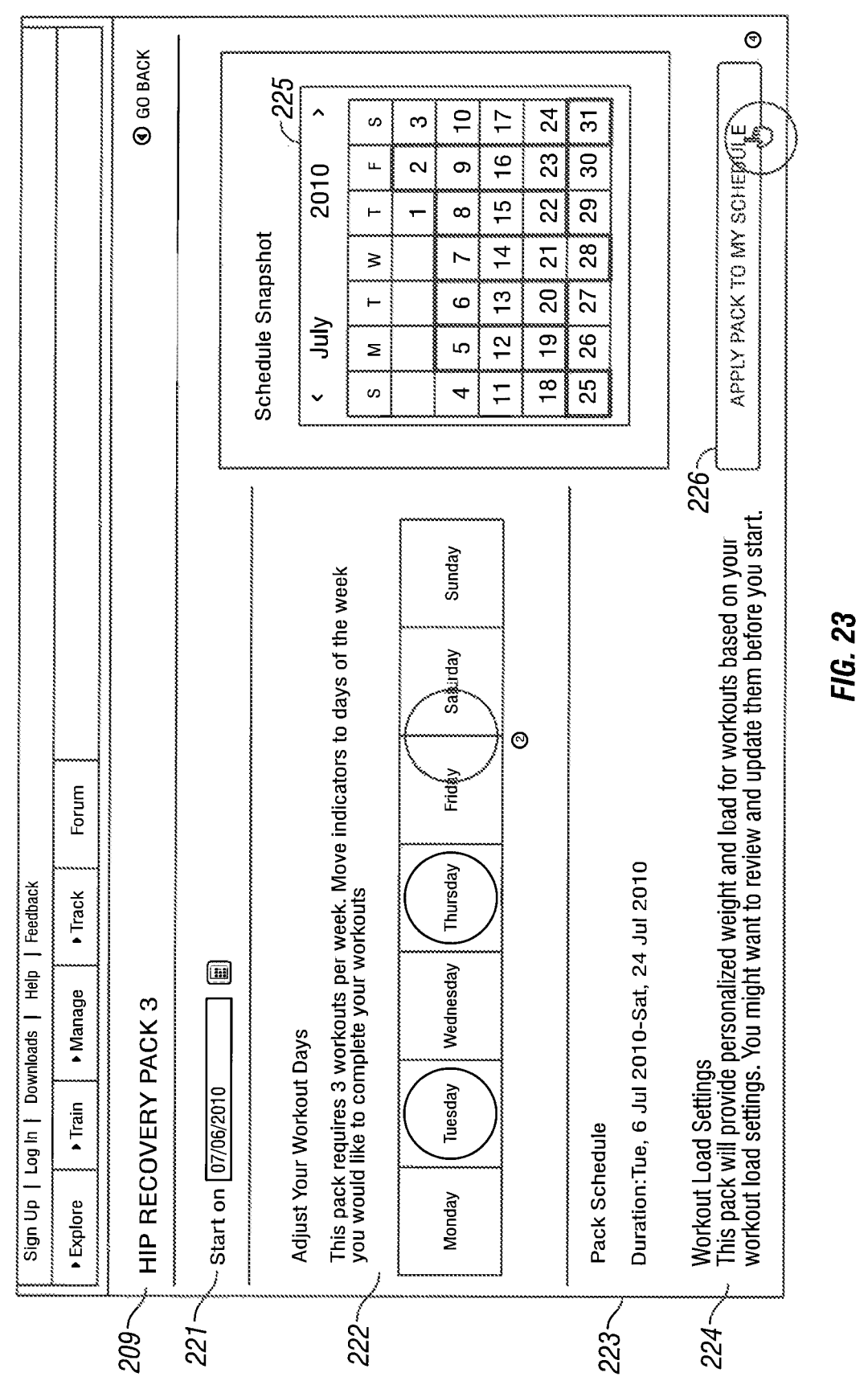
Figure 24:
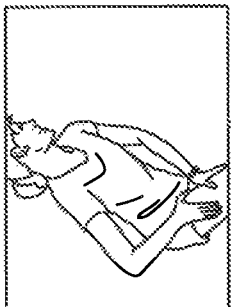
FIG. 24 is an exemplary GUI window for generating a workout schedule according to an embodiment of the present invention.

After the user has selected a particular training category 202 and a particular workout plan 206 and/or single workout 208, the user may manipulate a schedule button 220 and training module 200 may generate a schedule of a plurality of training activities corresponding to the training category. With reference to FIGS. 22-24, which are exemplary GUI windows according to an embodiment of the present invention, training module 200 may graphically display schedule information to the user. The schedule information may include date information 221, workout day indicator 222, a training duration 223, workout load settings 224, and a schedule snapshot 225.

The date information 221 includes start date and/or end date information for the group of training activities corresponding to the workout plan. In one embodiment, training module 200 may be adapted to allow the user to adjust the start date and/or end date of the training activities. After the user has defined the start date, the training duration 223 may be updated to graphically display the dates covered by the workout plan. For example, as shown in FIGS. 23 and 24, the training duration for the workout plan may be from Tuesday, 6 Jul. 2010 to Saturday, 24 Jul. 2010. In one embodiment, the training duration 223 may be dynamically updated as the date information 221 and/or workout day indicator 222 is adjusted.

The workout day indicator 222 graphically presents the scheduled workout days corresponding to the training activities of the workout plan. For example, as shown in FIG. 23, training module 200 may schedule training activities on Tuesdays, Thursdays, and Fridays, based on a workout plan requirement of three training activities per week. In one embodiment, training module 200 may be adapted to allow the user to select and move a day indicator to thereby adjust the days of the week for completing the training activities. For example, as shown in FIG. 23, a user may change a desired workout day from Fridays to Saturdays by dragging the day indicator to the desired workout day. As shown in FIG. 24, the user may manipulate the workout day indicator 222 as check boxes for selecting the scheduled workout days.

The workout load settings 224 graphically presents the resistance settings (load, time, and/or repetitions) for the training activities of the workout plan. If a user wishes to adjust the load settings for one or more training activities the user may select to update the settings and employ a workout load wizard 227, as shown for example in FIG. 25. The workout load wizard 227 may comprise a pop-up window that is adapted to accept user input regarding the desired load settings for one or more training activities. In this manner, the workout load wizard 227 may provide an initial self-assessment for the user. In one embodiment, the workout load wizard 227 may query the user regarding his or her current abilities with respect to a load setting. For example, the workout load wizard 227 may query the maximum weight the user may be comfortable with for a particular body movement and repetition level. Based on this input, training module 200 may update the load or resistance goals for a particular scheduled training activity. In one embodiment, the workout load wizard 227 may be employed when a user is scheduling a strength based workout plan or workout for the first time. In this manner, the user response to load setting queries may set the initial load settings for one or more of the training activities. In some embodiments, system defaults based on user personal or performance information may be used where the user fails to respond to a query. In one embodiment, the queries provided by the workout load wizard 227 are based on the selected training category 202, workout plan 206, and/or single workout 208. For example, the workout load wizard 227 may provide questions to the user tailored for a Get Strong workout 208 that different than questions that may be provided for a Hip Flex workout 208.

The workout schedule snapshot 225 graphically represents the scheduled training activities for the user. The scheduled training activity days may be dynamically updated as the user adjusts the date information 221 and/or workout day indicator 222. After the user has made any necessary adjustments to the scheduled training activities of the workout plan, the user may apply these training activities to his or her workout schedule 230 by clicking on the update schedule button 226.

Figure 26:
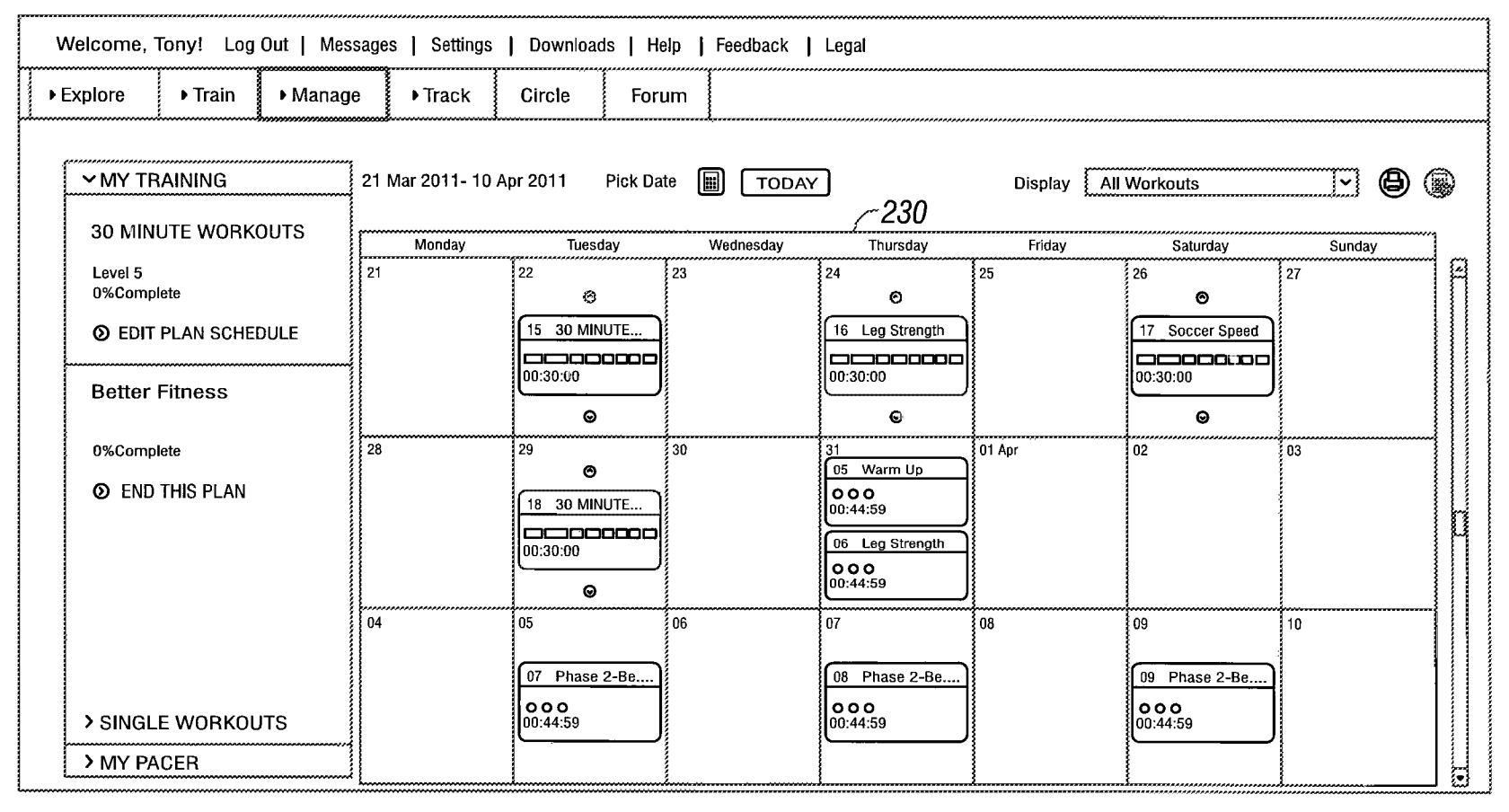
Figure 27:
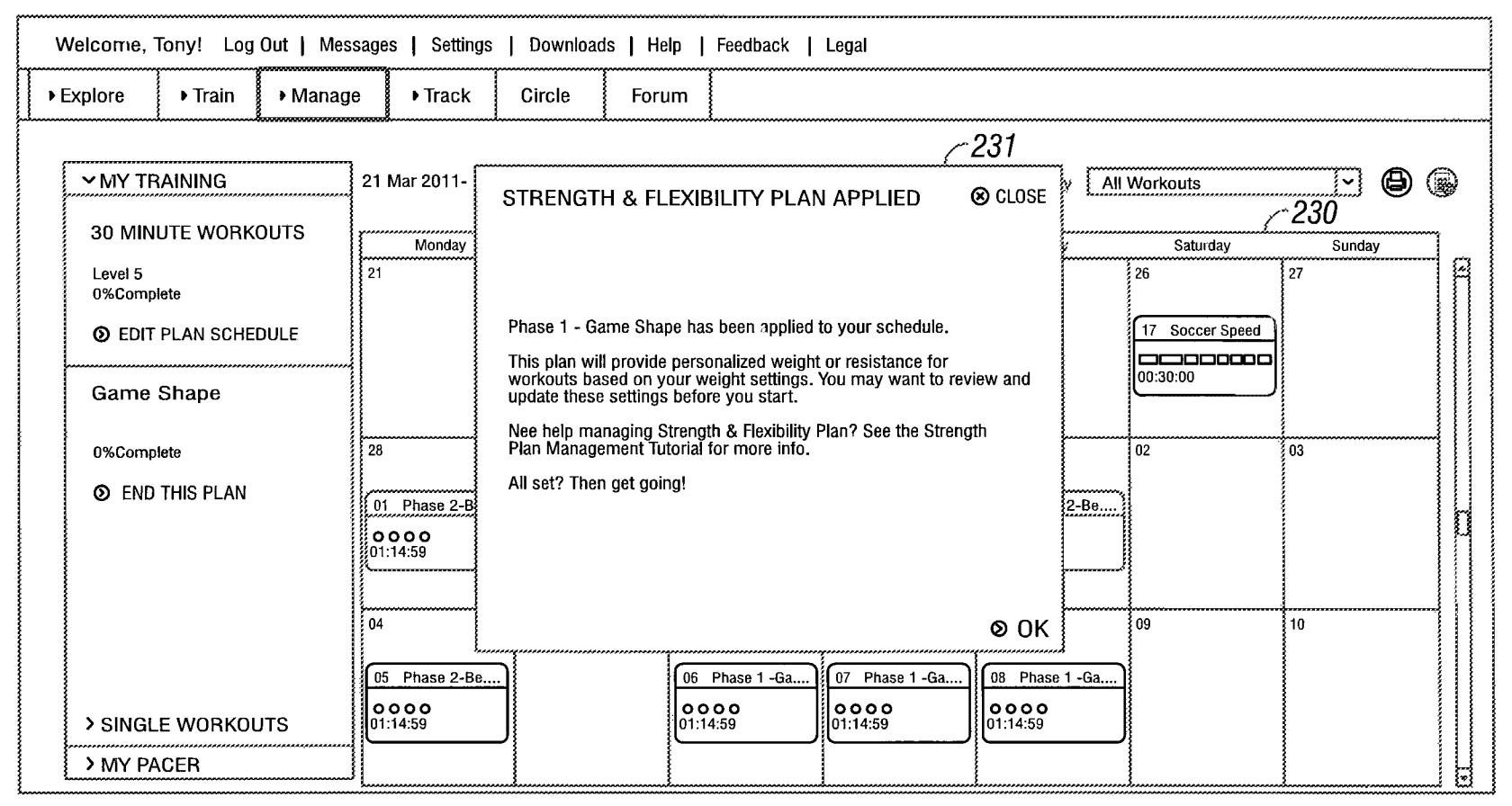
Figure 28:
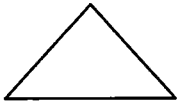
FIG. 28 is an exemplary GUI window according to an embodiment of the present invention.

After successful application of a workout plan including a plurality of training activities or a single workout to the user's schedule, the user may be brought to a view of his or her workout schedule 230, which may include previously scheduled training activities. FIG. 26 shows an exemplary GUI window displaying an updated user workout schedule 230. The workout schedule 230 may simultaneously display the user's scheduled workouts, including cardio and non-cardio based workout plan workouts and/or single workouts. In one embodiment, as shown in FIG. 27, a confirmation pop-up window confirming the application of the workout training activities or single workout training activity to the schedule. For example, as shown in FIG. 27, training module 200 may confirm that Hip Recovery Pack 3 has been applied to the user schedule. In one embodiment, the user may access a tutorial (e.g., a video) 232 for managing the completion of the training activities of the workout plan. FIG. 28 is an exemplary GUI pop-up window providing the management tutorial 232.

The updated user workout schedule 230 may be generated such that a newly added single workout or newly added workout plan training activities are synchronized with previously scheduled training activities. For example, the schedule 230 may be generated based on the schedule of individual cardio-based workouts that were previously scheduled according to the plan module 401 and schedule module 402, as described in commonly owned U.S. patent application Ser. No. 12/468,025, entitled "Program Products, Methods, and Systems for Providing Fitness Monitoring Services," and U.S. patent application Ser. No. 12/836,421, entitled "Fitness Monitoring Methods, Systems, and Program Products, and Applications Thereof," the disclosures of which are incorporated by reference thereto in their entirety.

In one embodiment, the updated user workout schedule 230 may be generated such that a newly added single workout or newly added workout plan training activities are synchronized with previously scheduled training activities based on a set of scheduling rules. In one embodiment, a schedule may be generated such that a non-cardio based training activity is not scheduled for the same day as a cardio training activity. For example, during scheduling of a workout plan that includes a strength based training activity scheduled for the same day as a cardio training activity, the schedule 230 may be adjusted such that the strength based training activity is adjusted for the next available day. For a selected soccer training category 202, for example, this scheduling may be advantageous to allow a user to rest certain muscle groups (e.g., the leg muscle groups after a Leg Strength training activity). In another embodiment, a schedule may be generated such that a strength based training activity is scheduled for the same day as a cardio training activity. For example, as shown in FIG. 26, a strength based Leg Strength training activity may be scheduled for execution immediately after a Warm Up cardio training activity.

One or more non-cardio based training activity may be scheduled in combination with one or more previously scheduled cardio based training activities. In one embodiment, the user may not be permitted to schedule a non-cardio based training activity unless at least one cardio based training activity is on the user's schedule.

In one embodiment, a single non-cardio based training activity may be scheduled in combination with a cardio based training activity. In one embodiment, a non-cardio based workout plan, including a plurality of non-cardio based training activities, may be scheduled in combination with a cardio based training activity. In one embodiment, a non-cardio based workout plan, including a plurality of non-cardio based training activities, and a single non-cardio based training activity may be scheduled in combination with a cardio based training activity. In one embodiment, a single non-cardio based training activity may be scheduled in combination with a scheduled non-cardio based workout plan, including a plurality of non-cardio based training activities.

Both non-cardio based training activities (e.g., strength based training activities) and cardio-based training activities may be applied to the user's workout schedule 230 based on the selected training category 202 and/or the user's other needs and goals. For example, in one embodiment, after a user has selected a soccer training category 202, an individual strength based training activity (e.g., Leg Strength) may be scheduled before a difficult cardio-based training activity. In this manner, training module 200 may prepare the user for the rigors of soccer (e.g., stamina and leg strength).

After completing a particular workout, training module 200 may permit a user to assign the workout as complete if they carried out the workout as defined. The training module 200 may present the user with one or more GUI windows that prompt the user to save or discard the recorded performance information associated with the workout. If the user decides to save their recorded performance information, a summary of their performance may be displayed. In one embodiment, the athlete may complete the workout according to the workout recording sub-module of the go module 1100, as described in commonly owned U.S. patent application Ser. No. 12/836,421, entitled "Fitness Monitoring Methods, Systems, and Program Products, and Applications Thereof," the disclosure of which is incorporated by reference thereto in its entirety.

Figure 29:
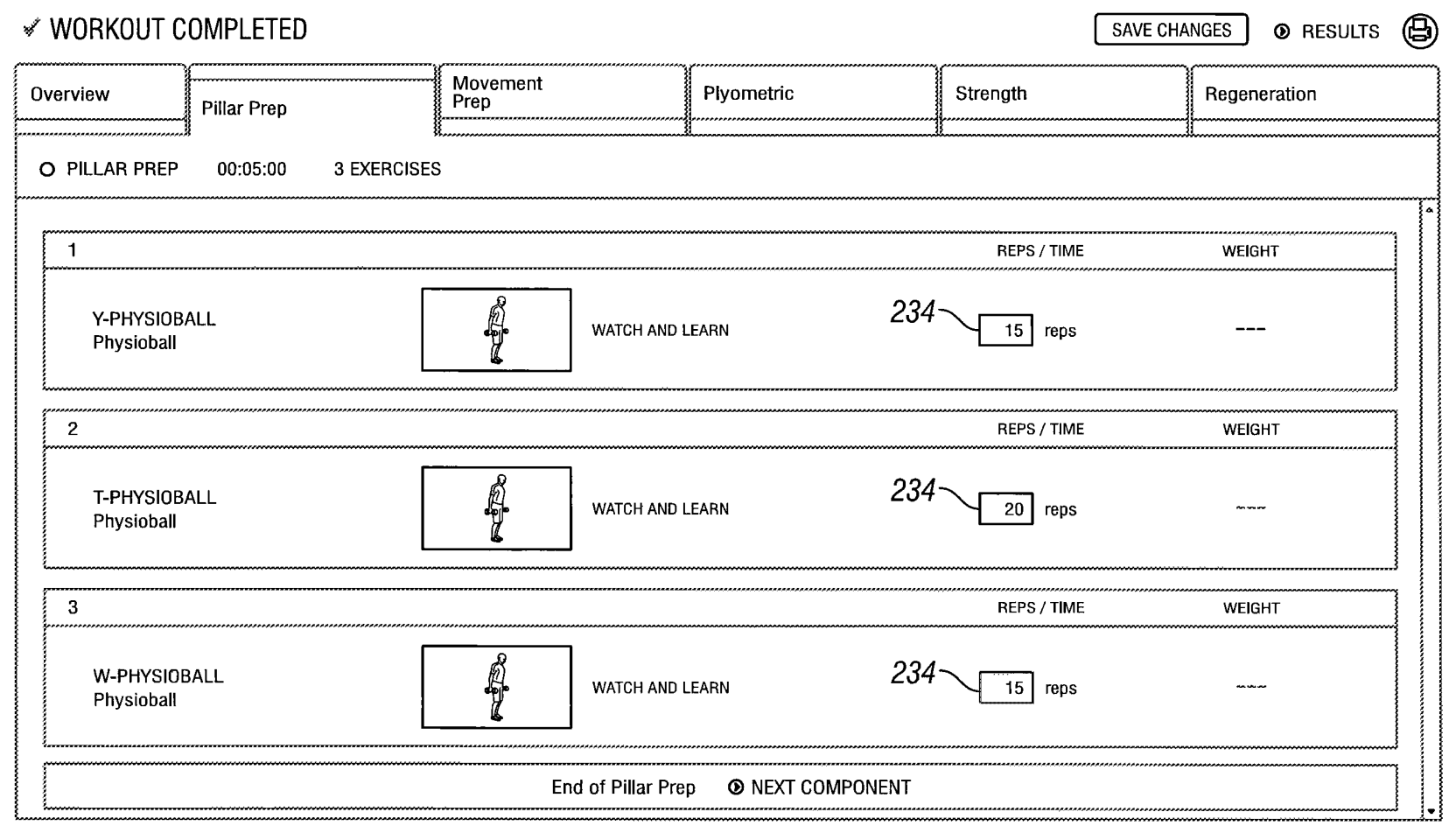
Figure 30:
FIG. 30 is an exemplary GUI window for user input of actual completed workout data according to an embodiment of the present invention.

In one embodiment, a user may enter actual workout data 234 related to a completed workout. With reference to FIGS. 29 and 30, if the workout comprises a strength-based training activity having a resistance goal—such as, for example, a load, repetition, and/or time goal—the user may enter actual time completed, and load and repetition volume completed if they vary from the amounts defined by the workout. For example, as shown in FIG. 29, a user may enter the actual repetitions 234 completed during a physioball exercise. In one embodiment, as shown in FIG. 30, other actual workout data including date, start time, and total workout time may be entered. These workout completion GUI windows may be presented to the user upon completion of a workout.

In one embodiment, if no data is entered, the scheduled time, repetition, or load goal will be assumed to have been completed. In one embodiment, when the athlete 100 completes a workout or chooses to end a workout early, the workout recording sub-module of the go module 1100 may prompt the athlete 100 to save or discard the recorded performance information associated with the workout. If the athlete 100 decides to save their recorded performance information, a summary of their performance may be displayed.

In one embodiment, the user's progression of resistance goals (e.g., load, time and/or repetitions) may be tracked and used to adjust the resistance requirements for upcoming scheduled training activities. This, in turn, may help the user achieve desired fitness goals by progressively building the user's strength, for example. Based on the user's progression of resistance goals, including the input of load, repetition, and/or time data entered by the user, the resistance goals for upcoming training activities may be defined by a resistance sub-module 201, as shown in FIGS. 8 and 9 for example. In this manner, user resistance goals may be dynamically adjusted and influenced by completed requirements.

In one embodiment, the actual resistance data 234 entered by the user after an activity may be used to schedule the appropriate load, repetition, and/or time goals for an upcoming training activity. The workout completion GUI windows shown in FIGS. 29 and 30 may be presented to the user upon completion of a workout to assess the user's current fitness level and provide any necessary resistance goal adjustment. Based on the user input, the resistance sub-module 201 may define one or more resistance goals.

In one embodiment, the resistance goal completed and entered by the user may be stored by resistance sub-module 201. This value may be later viewed and modified, if necessary, by the user. If the user has entered a completed resistance goal for a training activity that is equal to the scheduled resistance goal, then resistance sub-module 201 may incrementally increase that resistance goal for a future training activity by a predetermined percentage multiplied by the scheduled (and completed) resistance goal. In one embodiment, resistance sub-module 201 may also incrementally increase the resistance goal for a future training activity if the user has entered a completed resistance goal for the completed training activity that is within a predetermined percentage of the scheduled resistance requirement.

In one embodiment, all scheduled non-cardio training activities have predetermined resistance goals. In an alternative embodiment, the resistance goal for each non-cardio training activity is based on the completion of a previous training activity resistance goal and/or user input about the previous training activity. In one embodiment, if a user has entered a completed resistance goal for a training activity that differs from the scheduled resistance goal for that training activity, resistance sub-module 201 may define the resistance goals for one or all future scheduled training activities for the user that include a resistance goal based on the user input. In one embodiment, the user's resistance requirements for scheduled training activities may be adjusted based on the user's completion of other training activities, including cardio based training activities.

Figure 31:
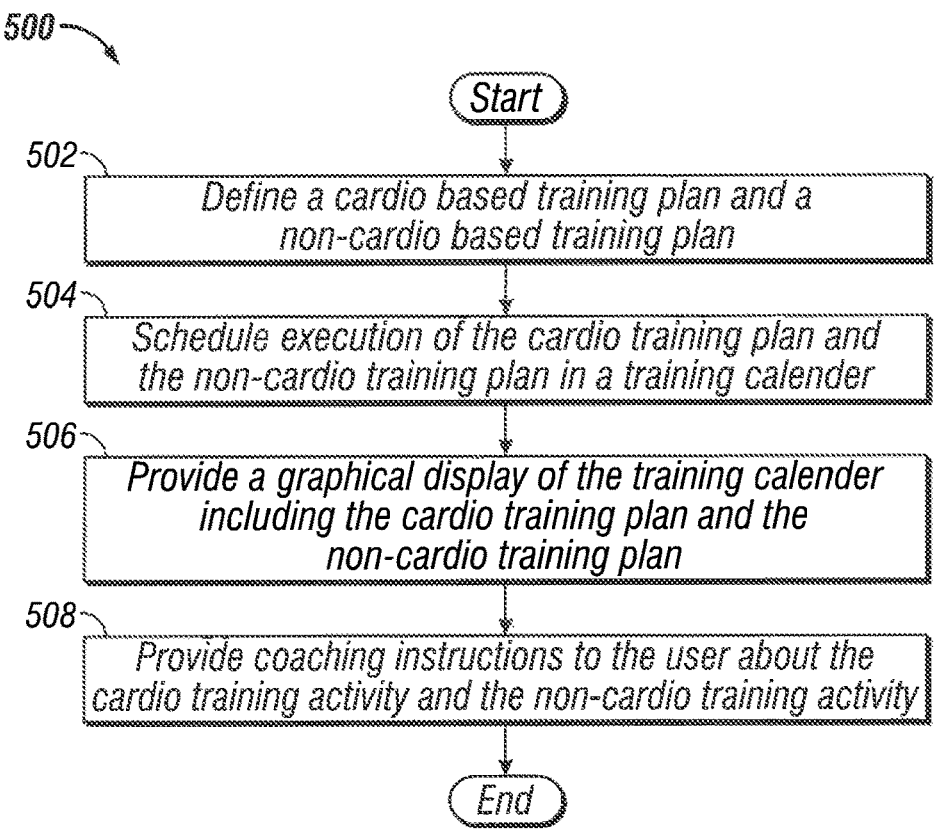
FIG. 31 is a process flowchart of a method for scheduling training activities for a user of a fitness monitoring device according to an embodiment of the present invention.

One or more methods for scheduling training activities for an athlete 100 may be carried out by employing a portable fitness monitoring device 102, a computer server system 112, and/or a personal computer 114, as described above. FIG. 31 is a process flowchart of an exemplary method 500 for scheduling training activities for a user of a fitness monitoring device and methods according to an embodiment of the present invention. Method 500 includes at least steps 502, 504, 506 and 508 carried out by at least one processor. Method 500 begins in step 502, where the process starts by defining a cardio based training plan and a non-cardio based training plan. For example, as described above training module 200 may include a workout plan including one or more cardio-based training activities and one or more non-cardio based training activities. The cardio based training activities may include a cardio goal, such as, a pace goal, speed goal, a heart rate goal, or other suitable performance goal. The non-cardio based training activities may include a resistance goal or any other suitable performance goal. In one embodiment, the non-cardio based training plan may be a strength based training plan. In step 504, the process includes scheduling execution of the non-cardio based training plan and the cardio based training plan in a training calendar. For example, training module 200 may schedule training activities from a non-cardio based workout plan 206 in conjunction with a single cardio based workout 208. The training activities may be specifically geared toward a desired objective, e.g., a training category. In step 506, the process provides a graphical display of the training calendar 230 to the user including a schedule of the non-cardio based training plan and the cardio based training plan. In one embodiment, the process may further include providing coaching instructions to the user about the training activities, as shown, for example, in step 508. The coaching instructions may include, but is not limited to, providing descriptive text, instructional video and verbal feedback to the user before, during, or after the training activity.

Figure 32:
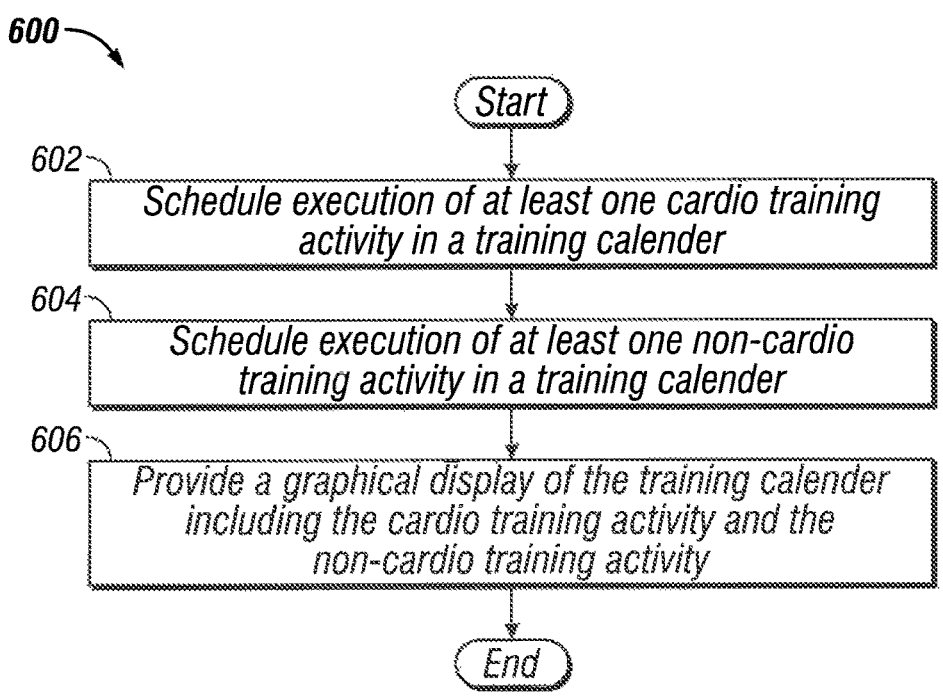
FIG. 32 is a process flowchart of a method for scheduling training activities for a user of a fitness monitoring device according to an embodiment of the present invention.

FIG. 32 is a process flowchart of an exemplary method 600 for scheduling training activities for a user of a fitness monitoring device according to an embodiment of the present invention. Method 600 includes at least steps 602, 604, and 606 carried out by at least one processor. Method 600 begins in step 602 with scheduling execution of at least one cardio training activity in a training calendar. In step 604, at least one non-cardio training activity is scheduled in combination with the scheduled cardio training activity in the training calendar. In one embodiment, a single non-cardio based training activity may be scheduled in combination with the cardio based training activity. In one embodiment, a non-cardio based workout plan, including a plurality of non-cardio based training activities, may be scheduled in combination with the cardio based training activity. In one embodiment, a non-cardio based workout plan, including a plurality of non-cardio based training activities, and a single non-cardio based training activity may be scheduled in combination with the cardio based training activity. In one embodiment, a single non-cardio based training activity may be scheduled in combination with a scheduled non-cardio based workout plan, including a plurality of non-cardio based training activities. In step 606, the process provides a graphical display of the training calendar to the user including a schedule of the cardio based training activity and the non-cardio based training activity.

Figure 33:
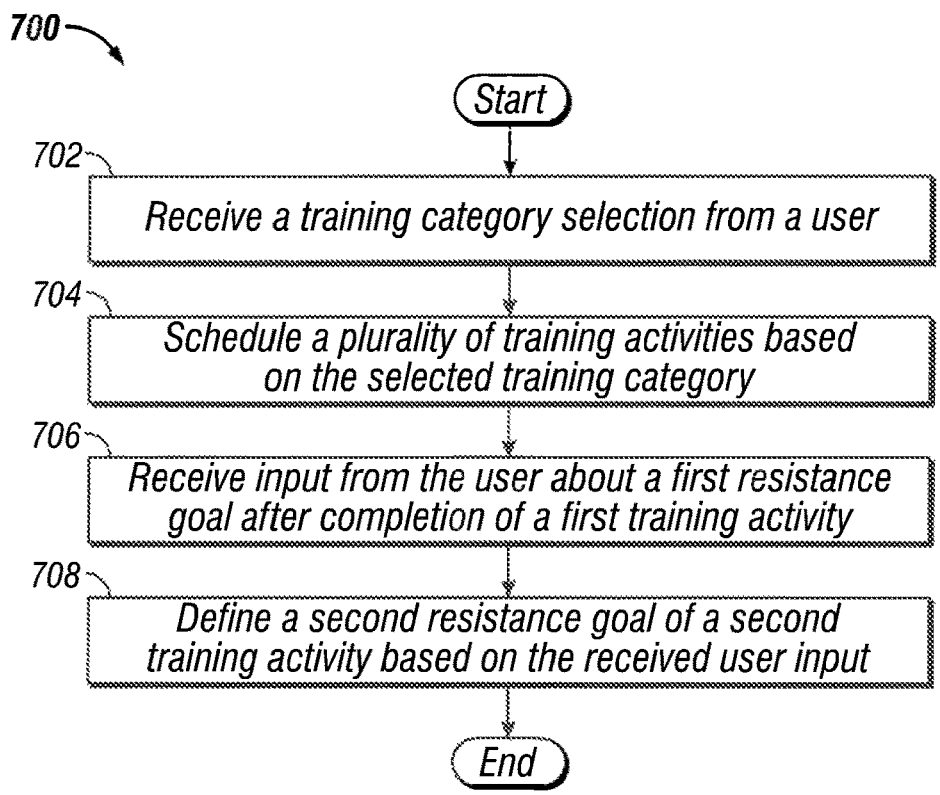
FIG. 33 is a process flowchart of a method for scheduling training activities for a user of a fitness monitoring device according to an embodiment of the present invention.

FIG. 33 is a process flowchart of an exemplary method 700 for scheduling training activities for a user of a fitness monitoring device and methods according to an embodiment of the present invention. Method 700 includes at least steps 702, 704, 706, and 708 carried out by at least one processor. Method 700 begins in step 702 with the selection of a training category. In one embodiment, the training categories 202 may correspond to one or more particular sports. For example, a user who wishes to train for soccer may select a soccer training category at the fitness monitoring device via a mobile application or website. The selection of a focused training category may facilitate scheduling of training activities which prepare the user for the rigors of soccer (e.g., stamina and leg strength). In other embodiments, training categories 202 also may be directed to broad fitness categories, the selection of which may facilitate scheduling of appropriate fitness activities.

In step 704, the process includes scheduling a plurality of training activities based on the selected training category. For example, a soccer training category may include a combination of cardio based training activities and non-cardio based activities (e.g., a strength based activity). In one embodiment, an individual strength based training activity (e.g., Leg Strength) may be scheduled in combination with a cardio-based training activity (e.g., a 30 minute hill workout). The combination of scheduled training activities may prepare the user for the rigors of soccer (e.g., stamina and leg strength). At least one training activity may require execution of a plurality of body movements with a corresponding resistance goal. The resistance goal may include, for example, a load goal, a repetition goal, and/or a time goal.

In step 706, the process includes receiving input about the resistance goal after completion of the training activity. The input may be made from the user or may be generated automatically from a external source, such as fitness machine 2100 or console gaming system 2000 described below. The input may include input that the resistance goal was completed by the user or that the resistance goal was not completed and the actual resistance requirement completed. In one embodiment, the input may be received at the server 112 from the fitness monitoring device 102. In step 708, the process defines a resistance goal for a subsequent training activity based on the user input. The process may incrementally increase (or decrease) the resistance goal for the subsequent training activity from the previous resistance goal when the user completed that goal (or did not complete the goal). The resistance goal for the subsequent training activity may be presented to the user before completion of the activity. For example, this resistance goal may appear in an updated training plan.

In one embodiment, the process may provide coaching to the user during the training activity. For example, during the activity, the portable fitness monitoring device 102 may send, for example, real-time performance information to the server 112, and in response the server 112 may send, for example, real-time feedback or coaching to the portable fitness monitoring device 102. In one embodiment, this communication during the activity may occur as a result of and/or simultaneously with the execution of a workout routine by the portable fitness monitoring device 102. After the activity, the portable fitness monitoring device 102 may send, for example, complete activity performance information to the server 112, and in response the server 112 may send, for example, post-activity analysis to the portable fitness monitoring device 102. For activities that require a corresponding resistance goal, after the activity the user may enter the actual load, time, and/or repetition completed.

Figure 34:
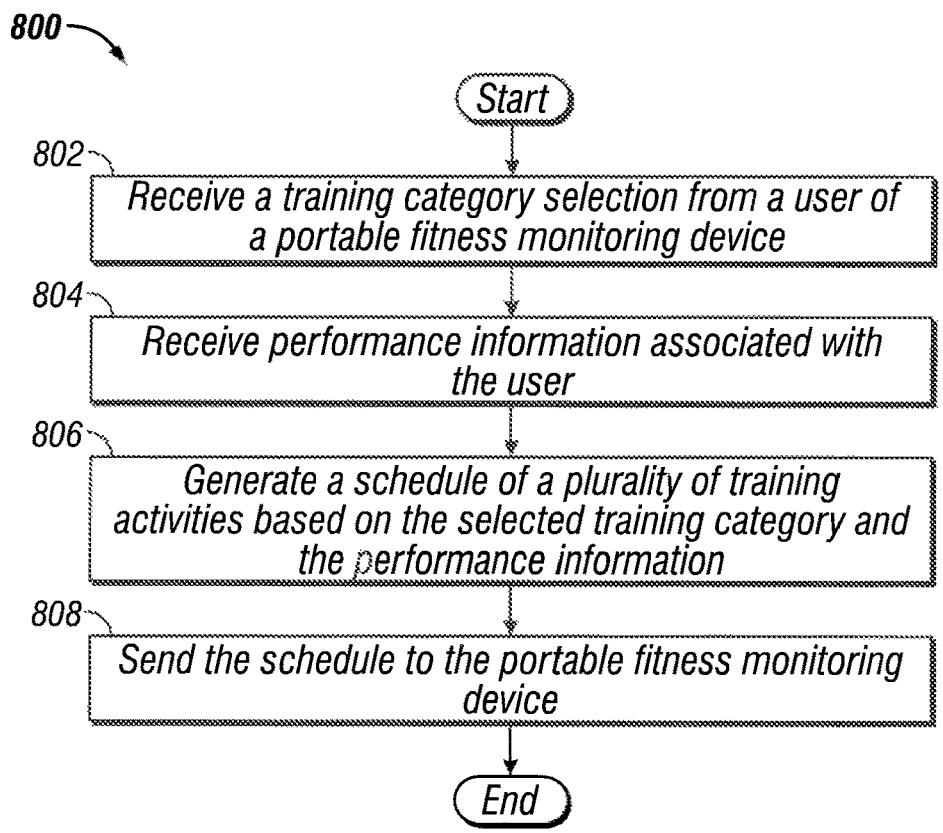
FIG. 34 is a process flowchart of a method for scheduling training activities for a user of a fitness monitoring device according to an embodiment of the present invention.

FIG. 34 is a process flowchart of an exemplary method 800 for generating a workout routine for a user of a fitness monitoring device and methods according to an embodiment of the present invention. Method 800 includes at least steps 802, 804, 806, and 808 carried out by at least one processor. Method 800 begins in step 802 with receiving a training category selection from a user of a portable fitness monitoring device. For example, a user who wishes to train for soccer may select a soccer training category 202 from a website or GUI window from a portable fitness monitoring device 102. The soccer training category 202 may allow the user to schedule training activities, including a combination of cardio based training activities and strength based activities, which may prepare the user for the rigors of soccer (e.g., stamina and leg strength). The process continues in step 804 with receiving performance information associated with the user from the portable fitness monitoring device. For example, from the portable fitness monitoring device 102 the user may provide performance information, such as a pace goal or resistance goal, that was recorded by the portable fitness monitoring device during a training activity previously conducted by the user or was input by the user after the activity. The performance information may also comprise information related to training activities that have not yet been completed. For example, the user may provide input in response to prompts or questions, such as, the desired amount of load resistance or repetitions to be completed. In step 806, the process generates a schedule of a plurality of training activities based on the selected training category and the performance information. In one embodiment, a first scheduled training activity includes a cardio goal and a second scheduled training activity includes a resistance goal. In step 808, the process sends the schedule including the scheduled training activities having a cardio goal and a resistance goal to the portable fitness monitoring device.

Figure 35:
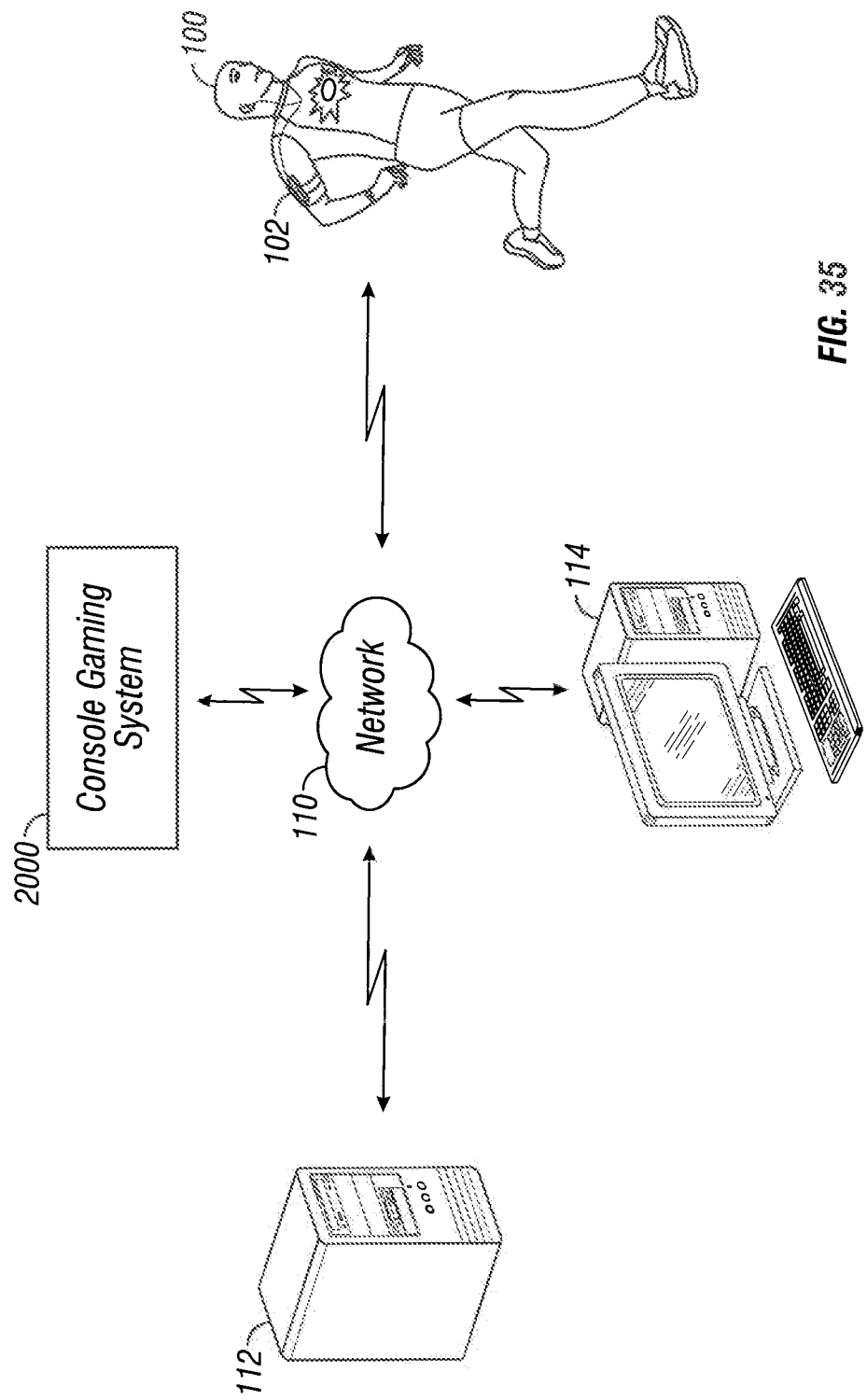
FIG. 35 is an illustration of a fitness monitoring device and a training module in communication with a gaming system according to an embodiment of the present invention.

In one embodiment, as shown in FIG. 35, fitness monitoring device 102 and training module 200 may be used in conjunction with a console gaming system 2000 adapted for movement detection, such as, for example, a Playstation 3, XBOX 360, or Nintendo® Wii gaming system. As will be appreciated by those of ordinary skill in the art, console gaming system 2000 may include software and hardware (e.g., a motion detection controller, camera, etc.) to recognize the movements of the user. Training module 200 may be configured to create and schedule console gaming system based workouts which may then be performed in conjunction with the console gaming system 2000. For example, a console gaming system based workout, such as, for example, a dancing based video game that requires specific body movements for successful completion, may be performed in front of the user's television. Training module 200 may be configured to communicate with the console gaming system 2000 and may receive user workout data. For example, console gaming system 2000 may provide data related to the number of movements the user completed successfully. Training module 200 may be configured to communicate with the console gaming system 2000 and may receive user workout data from the console. In this manner, console gaming system 2000 may provide input whether a performance goal was completed or not completed by the user.

In one embodiment, as shown in FIG. 36, fitness monitoring device 102 and training module 200 may be used in conjunction with a fitness machine 2100, such as, for example, a treadmill or weight lifting machine. Fitness monitoring device 102 and/or server 112 may be configured to communicate with the fitness machine 2100. In this manner, predetermined load settings based on the user's scheduled training activities may be sent to the fitness machine 2100 and the machine may automatically adjust the weights for the next exercise. In one embodiment, the user's schedule of training activities may also be sent to a plurality of fitness machines 2100 such that the machine required for a subsequent scheduled training activity may be preset when the user arrives at the machine. Training module 200 may be configured to communicate with the fitness machine 2100 and may receive user workout data from the machine. For example, fitness machine 2100 may provide data related to the number of movements the user completed successfully.

Various aspects of the present invention, or any parts or functions thereof, may be implemented using hardware, software, firmware, tangible computer readable or computer usable storage media having instructions stored thereon, or a combination thereof and may be implemented in one or more computer systems or other processing systems.

Program products, methods, and systems for providing fitness monitoring embodiments of the present invention can include any software application executed by one or more computing devices. A computing device can be any type of computing device having one or more processors. For example, a computing device can be a workstation, mobile device (e.g., a mobile phone, personal digital assistant, tablet computer, or laptop), computer, server, computer cluster, server farm, game console, set-top box, kiosk, embedded system, a gym machine, a retail system or other device having at least one processor and memory. Embodiments of the present invention may be software executed by a processor, firmware, hardware or any combination thereof in a computing device.

In this document, terms such as "computer program medium" and "computer-usable medium" may be used to generally refer to media such as a removable storage unit or a hard disk installed in hard disk drive. Computer program medium and computer-usable medium may also refer to memories, such as a main memory or a secondary memory, which can be memory semiconductors (e.g., DRAMs, etc.). These computer program products provide software to computer systems of the present invention.

Computer programs (also called computer control logic) may be stored on main memory and/or secondary memory. Computer programs may also be received via a communications interface. Such computer programs, when executed, may enable computer systems of the present invention to implement embodiments described herein. Where embodiments are implemented using software, the software can be stored on a computer program product and loaded into a computer system using, for example, a removable storage drive, an interface, a hard drive, and/or communications interface.

Based on the description herein, a person skilled in the relevant art will recognize that the computer programs, when executed, can enable one or more processors to implement processes described above, such as the steps in the methods illustrated by the figures. In an embodiment, the one or more processors can be part of a computing device incorporated in a clustered computing environment or server farm. Further, in an embodiment, the computing process performed by the clustered computing environment may be carried out across multiple processors located at the same or different locations.

Software of the present invention may be stored on any computer-usable medium. Such software, when executed in one or more data processing device, causes the data processing device to operate as described herein. Embodiments of the invention employ any computer-usable or -readable medium, known now or in the future. Examples of computer-usable mediums include, but are not limited to, primary storage devices (e.g., any type of random access or read only memory), secondary storage devices (e.g., hard drives, floppy disks, CD ROMS, ZIP disks, tapes, magnetic storage devices, optical storage devices, MEMS, nanotechnological storage devices, memory cards or other removable storage devices, etc.), and communication mediums (e.g., wired and wireless communications networks, local area networks, wide area networks, intranets, etc.).

Embodiments have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The present invention has been described above by way of exemplary embodiments. Accordingly, the present invention should not be limited by any of the above-described exemplary embodiments, but should be defined only in accordance with the following claims and their equivalents.

What is claimed is:

1. A fitness monitoring system, comprising:
    a first fitness machine;
    a portable fitness monitoring device configured to communicate with the first fitness machine; and
    a training plan stored on the portable fitness monitoring device, the training plan comprising a plurality of scheduled training activities with predetermined load settings,
    wherein the portable fitness monitoring device is configured to send the predetermined load settings to the first fitness machine, and
    wherein the first fitness machine automatically adjusts the first fitness machine's load settings based on the predetermined load settings for one of the plurality of scheduled training activities,
    wherein the training plan is updated to include both aerobic and non-aerobic training activities, such that the fitness monitoring device generates a schedule that includes a graphical representation of a training calendar including each of those training activities, and
    wherein the schedule is generated by the portable fitness monitoring device such that a non-aerobic activity is not scheduled on the same day as the aerobic activity.

2. The system of claim 1, wherein the first fitness machine comprises a weight lifting machine.

3. The system of claim 1, further comprising a server configured to communicate with the portable fitness monitoring device.

4. The system of claim 3, wherein the server is configured to communicate with the first fitness machine.

5. The system of claim 3, wherein the portable fitness monitoring device is configured to communicate with the first fitness machine via the server.

6. The system of claim 1, further comprising a second fitness machine, wherein the portable fitness monitoring device is configured to communicate with the second fitness machine.

7. The system of claim 6, wherein the portable fitness monitoring device is configured to send the training plan to the first fitness machine and the second fitness machine, and wherein the second fitness machine is preset for a subsequent scheduled training activity when a user arrives at the second fitness machine.

8. The system of claim 1, wherein the portable fitness monitoring device is configured to receive workout data associated with a user from the first fitness machine.

9. The system of claim 8, wherein the workout data comprises a number of movements the user completed successfully.

10. The system of claim 8, wherein the portable performance monitoring device is configured to define a resistance goal for a subsequent scheduled training activity based on the workout data.

11. A method of scheduling a plurality of training activities for a user of a portable fitness monitoring device, the method comprising:
    receiving at the portable fitness monitoring device a training category selection from the user;
    scheduling a plurality of training activities including both aerobic and non-aerobic activities based on the selected training category, wherein a first training activity comprises predetermined load settings, wherein the scheduling further includes generating a schedule such that non-aerobic activities are not scheduled on the same day as the aerobic activities;
    sending the predetermined load settings from the portable fitness monitoring device to a first fitness machine; and
    automatically adjusting the load settings of the first fitness machine based on the predetermined load settings.

12. The method of claim 11, wherein the first fitness machine comprises a weight lifting machine.

13. The method of claim 11, wherein sending the predetermined load settings from the portable fitness monitoring device to the first fitness machine comprises sending the predetermined load settings via a server.

14. The method of claim 11, further comprising sending the schedule of the plurality of training activities to the first fitness machine and a second fitness machine;
    presetting the second fitness machine for a subsequent scheduled training activity before the user arrives at the second fitness machine.

15. The method of claim 11, further comprising receiving from the first fitness machine the user's workout data associated with the first training activity.

16. The method of claim 15, wherein the user's workout data comprises a number of movements the user completed successfully.

17. The method of claim 15, further comprising defining a resistance goal for a subsequent scheduled training activity based on the user's workout data.

18. The method of claim 17, wherein the resistance goal comprises a repetition goal.

19. The method of claim 17, wherein the resistance goal comprises a load goal.

20. The method of claim 17, wherein the resistance goal comprises an incremental increase from a previously completed resistance goal.

\* \* \* \* \*